United States Patent [19]
Rane et al.

[11] Patent Number: 5,939,416
[45] Date of Patent: Aug. 17, 1999

[54] BENZO (5,6) CYCLOHEPTAPYRIDINE COMPOUNDS USEFUL AS FARNESYL PROTEIN TRANSFERASE INHIBITORS

[75] Inventors: Dinanath F. Rane, Morganville; Stacy W. Remiszewski, Washington Township; Ronald J. Doll, Maplewood, all of N.J.

[73] Assignee: Schering Corporation, Kenilworth, N.J.

[21] Appl. No.: 08/877,366

[22] Filed: Jun. 17, 1997

[51] Int. Cl.[6] ...................... A61K 31/535; A61K 31/445; C07D 413/14; C07D 401/14
[52] U.S. Cl. .................. 514/228.8; 514/290; 544/96; 546/93
[58] Field of Search ............................ 546/93; 544/126, 544/300, 96; 514/255, 232.8, 290, 228.8

[56] References Cited

U.S. PATENT DOCUMENTS

| | | |
|---|---|---|
| 5,151,423 | 9/1992 | Piwinski et al. . |
| 5,696,121 | 12/1997 | Bishop .................................... 514/254 |
| 5,714,609 | 2/1998 | Doll et al. . |
| 5,719,148 | 2/1998 | Bishop et al. . |
| 5,721,236 | 2/1998 | Bishop et al. . |
| 5,728,703 | 3/1998 | Bishop et al. . |

FOREIGN PATENT DOCUMENTS

WO95/10516  4/1995  WIPO .

OTHER PUBLICATIONS

J. Chem. Research (S) (1996), pp. 430–431.

Synth. Comm., 25, 15 (1995), pp. 2285–2294.

Bull. Chem. Soc., (1968), pp. 974–979.

Synth. Comm., 22, 16 (1992), pp. 883–891.

Tetrahedron, (1987), pp. 4377–4383.

Chem. Abstr., 53 (1959), col. 8111.

Chem. Abstr., 53 (1959), col. 21940.

Kjosravi–Far R et al. Cell Growth & Differentiation. 3, pp. 461–469, Jul. 1992.

Primary Examiner—Evelyn Mei Huang
Attorney, Agent, or Firm—A. W. Magatti

[57] ABSTRACT

Compounds of the following formula useful for inhibiting Ras function and therefore inhibiting or treating the abnormal growth of cells are disclosed:

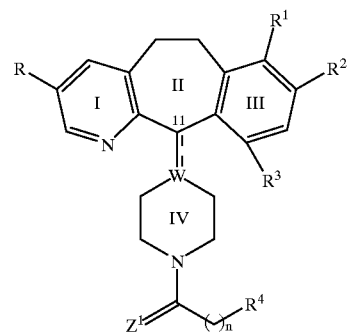

or an N-oxide thereof, or a pharmaceutically acceptable salt or solvate thereof, wherein:

R and $R^2$ are independently selected from halo;

$R^1$ and $R^3$ are independently selected from the group consisting of H and halo, provided that at least one of $R^1$ and $R^3$ is H;

$R^4$ is

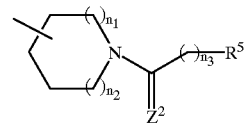

or $R^5$;

$R^5$ is

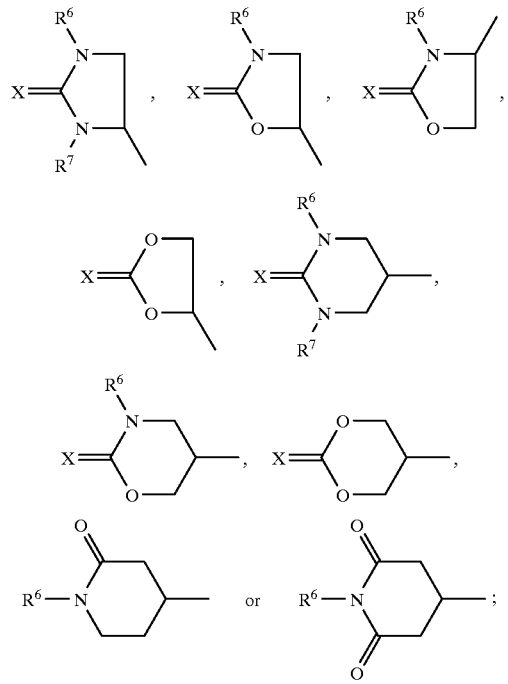

and the remaining variables are as defined in the specification.

13 Claims, No Drawings

BENZO (5,6) CYCLOHEPTAPYRIDINE COMPOUNDS USEFUL AS FARNESYL PROTEIN TRANSFERASE INHIBITORS

BACKGROUND

International Publication Number W095/10516, published Apr. 20, 1995 discloses compounds of the formula:

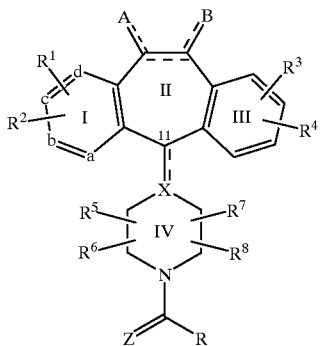

(1.0)

wherein R can be heterocycloalkyl-methyl attached to the carbon of the methylene group by a heteroatom, a substituted piperidinyl or substituted piperidinylmethyl. The compounds are said to be useful for inhibiting farnesyl protein transferase.

SUMMARY OF THE INVENTION

Compounds of the present invention are represented by Formula I:

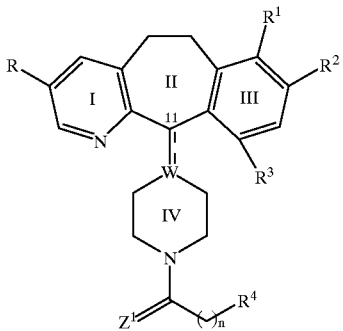

I or an N-oxide thereof, or a pharmaceutically acceptable salt or solvate thereof, wherein:

R and $R^2$ are independently selected from halo;

$R^1$ and $R^3$ are independently selected from the group consisting of H and halo, provided that at least one of $R^1$ and $R^3$ is H;

W is N, CH or C, when the double bond is present at the C-11 position;

$R^4$ is

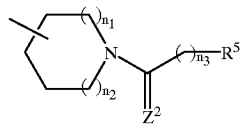

or $R^5$;

$R^5$ is

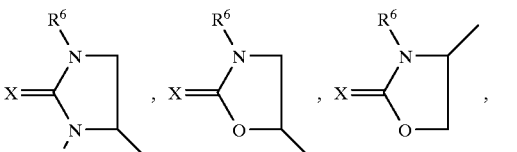

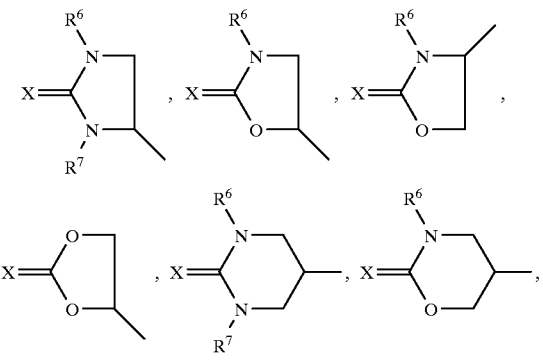

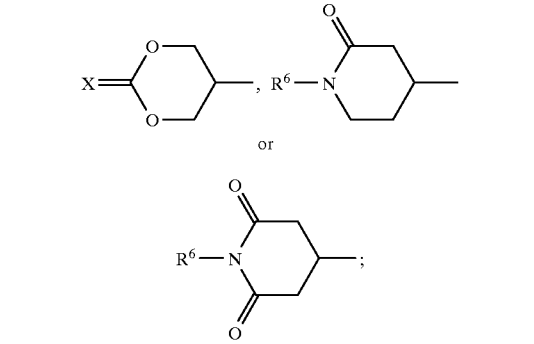

or

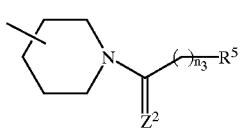

$R^6$ and $R^7$ are independently selected from the group consisting of H, alkyl, substituted alkyl, acyl, aryl, aralkyl, heterocycloalkyl and heteroaryl;

X is =O or =S;

$Z^1$ and $Z^2$ are independently =O or =S;

n and $n_3$ are independently 0, 1 or 2; and $n_1$ and $n_2$ are independently 0 or 1.

In the compounds of the invention, preferably R is Br, $R^2$ is halo and $R^1$ is halo; or R is Br, $R^2$ is halo and $R^3$ is halo; or R is Br, $R^2$ is halo and $R^1$ and $R^3$ are each H. $R^2$ is preferably Br or Cl. When $R^1$ or $R^3$ is halo, it is preferably Br or Cl. $Z^1$ is preferably =O. $Z^2$ is preferably =O. W is preferably CH. A preferred value for n is 1, and $n_3$ is preferably 0 or 1.

$R^4$ is preferably

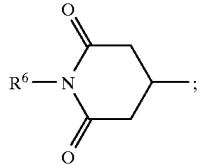

(i.e., $n_1$ and $n_2$ are each 1), or $R^5$. When present, the piperidinyl ring in $R^4$ is preferably attached to the rest of the molecule through the 4-position carbon ring member. Preferred $R^5$ groups are

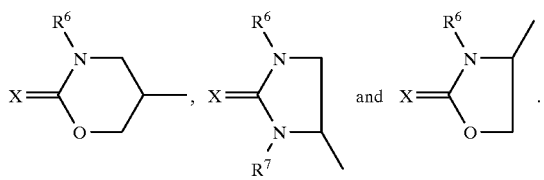

Preferred definitions for $R^6$ and $R^7$ are hydrogen. X is preferably =O.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. This invention further provides a method of inhibiting ras farnesyl protein transferase, in mammals, especially humans, by the administration of an effective amount of the tricyclic compounds described above. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount of a compound of this invention. Abnormal growth of cells refers to cell growth independent of normal regulatory mechanisms (e.g., loss of contact inhibition). This includes-the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth by administering an effective amount of the tricyclic compounds, described herein, to a mammal (e.g., a human) in need of such treatment. In particular, this invention provides a method for inhibiting or treating the growth of tumors expressing an activated Ras oncogene by the administration of an effective amount of the above described compounds. Examples of tumors which may be inhibited or treated include, but are not limited to, breast cancer, prostate cancer, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, Ick, and fyn), may be inhibited or treated by the tricyclic compounds described herein.

The tricyclic compounds useful in the methods of this invention inhibit or treat the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

MH$^+$ represents the molecular ion plus hydrogen of the molecule in the mass spectrum;

Bu represents butyl; Et represents ethyl; Me represents methyl; Ph represents phenyl;

alkyl (including the alkyl portions of alkoxy, alkylamino and dialkylamino) represents straight and branched carbon chains and contains from one to twenty carbon atoms, preferably one to six carbon atoms;

substituted alkyl represents alkyl as defined above substituted by 1 to 3 substituents independently selected from the group consisting of halo, hydroxy, alkoxy, phenoxy, $CF_3$, amino, alkylamino, dialkylamino, —COOR$^8$, wherein R$^8$ is H, alkyl, aryl or aralkyl (e.g., benzyl), or —NO$_2$;

acyl represents C(O)R$^9$, wherein R$^9$ is alkyl; ;aryl; alkoxy; aryloxy; heterocycloalkyl; heteroaryl; OR$^{10}$, wherein R$^{10}$ is alkyl, aryl, alkoxy, aryloxy, heterocycloalkyl or heteroaryl; NR$^{11}$R$^{12}$ where R$^{11}$ and R$^{12}$ are independently chosen from H and R$^{10}$;

aryl (including the aryl portion of aryloxy and aralkyl) represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, $CF_3$, amino, alkylamino, dialkylamino, —NO$_2$ or —COOR$^{13}$, wherein R$^{13}$ is H, alkyl, aryl or aralkyl (e.g., benzyl);

heterocycloalkyl represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S—or —NR$^{13}$—, wherein R$^{13}$ is as defined above; suitable heterocycloalkyl groups include 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, etc.;

heteroaryl represents cyclic groups, optionally substituted as defined above for aryl, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., triazolyl, 2-, 3- or 4-pyridyl or pyridyl N-oxide; and halo represents fluoro, chloro, bromo and iodo.

The following solvents and reagents may be referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); m-chloroperbenzoic acid (MCPBA); triethylamine (Et$_3$N); diethyl ether (Et$_2$O); ethyl chloroformate (ClCO$_2$Et); and 1-(3-dimethylaminopropyl)-3-ethyl carbodiimide hydrochloride (DEC).

Representative structures of Formula I with respect to W and the optional double bond are as follows:

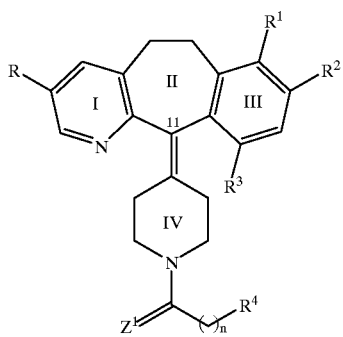

and

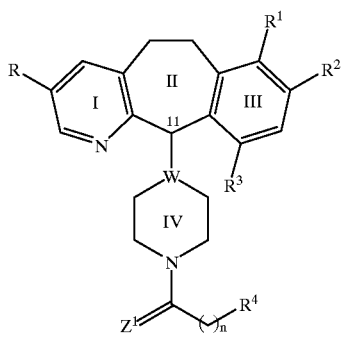

Lines drawn into the ring systems indicate that the indicated bond may be attached to any of the substitutable ring carbon atoms.

Certain compounds of the invention may exist in different isomeric (e.g., enantiomers, diastereoisomers and atropisomers) forms. The invention contemplates all such isomers both in pure form and in admixture, including racemic mixtures. Enol forms are also included.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyridonitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner.

The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purpopses of the invention.

Compounds of the invention may be made by the methods described in the examples below, and by using the methods described in WO 95/10516—see, for example, the methods for preparing compounds of Formula 400.00.

Compounds of the invention wherein $Z^1$ and $Z^2$ are =O can be prepared by reacting a compound of the formula II or III

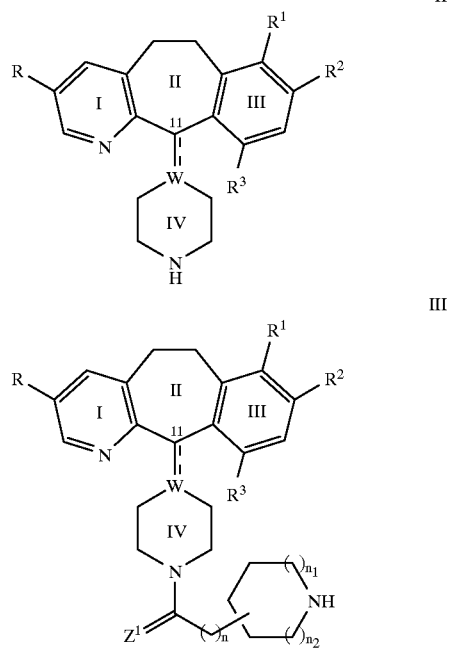

wherein all other substituents are as defined for Formula I, with an acid of formula HOOC—(CH$_2$)$_n$—R$^5$ or HOOC—(CH$_2$)$_{n3}$—R$^5$, respectively, wherein n, n$_3$ and R$^5$ are as defined above. The reaction is carried out using standard amide coupling conditions, for example the reaction can be carried out at room temperature, in an inert solvent such as DMF, in the presence of a condensing agent such as 1-(3-dimethylaminopropyl)-3-ethyl-carbodiimide hydrochloride, a base such as N-methylmorpholine and an activating agent such as 1-hydroxybenzotriazole.

Alternatively, compounds of formula I wherein R$^4$ is an oxazinone, for example a structure of the formula

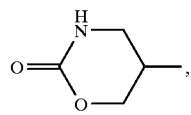

can be prepared by a rearrangement reaction: a compound of formula II can be reacted with 1-N-t- butoxycarbonylazetidinyl-3-acetic acid under the amide coupling conditions described above, and the resulting N-protected azetidine compound is reacted with an oxidizing agent such as ceric ammonium nitrate to obtain the desired oxazinone.

When $Z^1$, or $Z^1$ and $Z^2$, represent sulfur, a compound of formula I wherein $Z^1$, or $Z^1$ and $Z^2$, is oxygen is reacted with $P_2S_5$, Lawesson's reagent, or another reagent capable of introducing sulfur in place of oxygen. The reaction may take place at elevated temperature in pyridine, toluene or other suitable solvents. For compounds wherein $Z^1$ and $Z^2$ are different, the conversion form oxygen to sulfur can be effected before the starting materials (i.e., compounds of formula II and the acid) are reacted.

Compounds of formula I comprising a pyridyl N-oxide in ring I of the tricyclic portion can be prepared by procedures well known in the art. For example, the compound of formula II can be reacted with MCPBA in a suitable organic solvent, e.g., $CH_2Cl_2$ (usually anhydrous). at a suitable temperature, to obtain an N-oxide of formula IIa

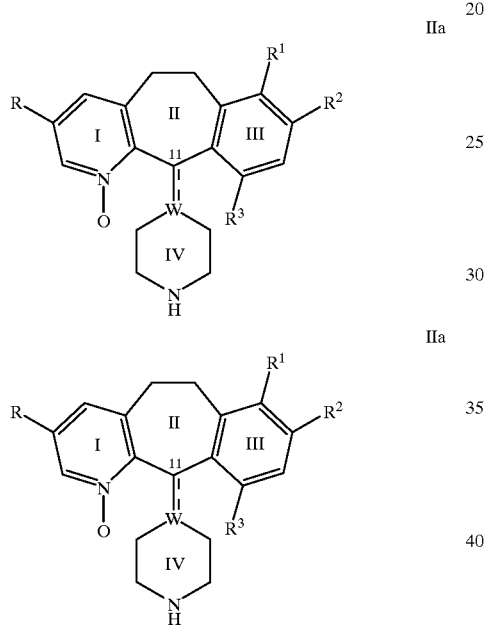

IIa

IIa

Generally, the organic solvent solution of formula II is cooled to about 0° C. before the MCPBA is added. The reaction is then allowed to warm to room temperature during the reaction period. The desired product can be recovered by standard separation means, for example, the reaction mixture can be washed with an aqueous solution of a suitable base, e.g., saturated $NaHCO_3$ or NaOH (e.g., i N NaOH), and then dried over anhydrous $MgSO_4$. The solution containing the product can be concentrated in vacuo, and the product can be purified by standard means, e.g., by chromatography using silica gel (e.g., flash column chromatography).

Compounds of formula II are prepared by methods known in the art, for example by methods disclosed in WO 95/10516, in U.S. 5,151,423 and those described below. Compounds of formula II wherein the C-3 postion of the pyridine ring in the tricyclic structure is substituted by bromo can also be prepared by a procedure comprising the following steps:

(a) reacting an amide of the formula

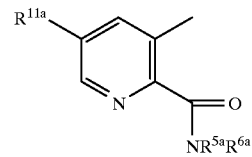

wherein $R^{11a}$ is Br, $R^{5a}$ is hydrogen and $R^{6a}$ is $C_1$–$C_6$ alkyl, aryl or heteroaryl; $R^{5a}$ is $C_1$–$C_6$ alkyl, aryl or heteroaryl and $R^{6a}$ is hydrogen; $R^{5a}$ and $R^{6a}$ are independently selected from the group consisting of $C_1$–$C_6$ alkyl and aryl; or $R^{5a}$ and $R^{6a}$, together with the nitrogen to which they are attached, form a ring comprising 4 to 6 carbon atoms or comprising 3 to 5 carbon atoms and one hetero moiety selected from the group consisting of —O— and —$NR^{9a}$—, wherein $R^{9a}$ is H, $C_1$–$C_6$ alkyl or phenyl; with a compound of the formula

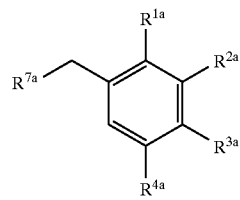

wherein $R^{1a}$, $R^{2a}$, $R^{3a}$ and $R^{4a}$ are are independently selected from the group consisting of hydrogen and halo and $R^{7a}$ is Cl or Br, in the presence of a strong base to obtain a compound of the formula

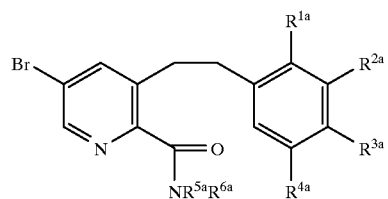

(b) reacting a compound of step (a) with
(i) $POCl_3$ to obtain a cyano compound of the formula

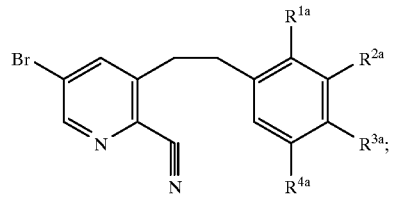

or (ii) DIBALH to obtain an adlyde of the formula

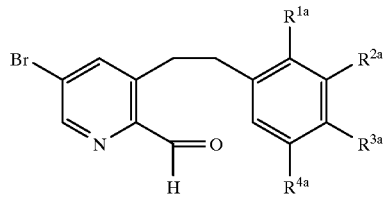

(c) reacting the cyano compound or the aldehyde with a piperidine derivative of the formula

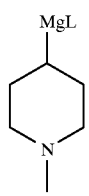

wherein L is a leaving group selected from the group consisting of Cl and Br, to obtain an aldehyde or an alcohol of the formula below, respectively:

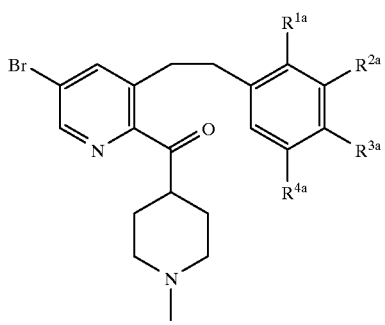

or

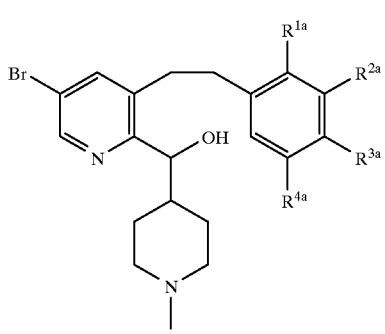

(d)(i) cyclizing the aldehyde with $CF_3SO_3H$ to obtain a compound of formula II wherein the dotted line represents a double bond; or (d)(ii) cyclizing the alcohol with polyphosphoric acid to obtain a compound of formula II wherein the dotted line represents a single bond.

Methods for preparing compounds of formula II disclosed in WO 95/10516, U.S. 5,151,423 and described below employ a tricyclic ketone intermediate. Such intermediates of the formula

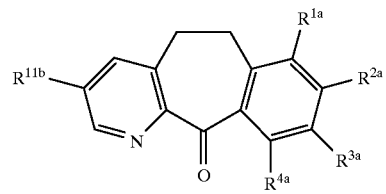

wherein $R^{11b}$, $R^{1a}$, $R^{2a}$, $R^{3a}$ and $R^{4a}$ are independently selected from the group consisting of hydrogen and halo, can be prepared by the following process comprising (a) reacting a compound of the formula

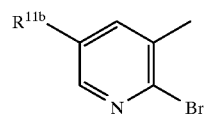

(i) with an amine of the formula $NHR^{5a}R^{6a}$, wherein $R^{5a}$ and $R^{6a}$ are as defined in the process above; in the presence of a palladium catalyst and carbon monoxide to obtain an amide of the formula:

(ii) with an alcohol of the formula $R^{10a}OH$, wherein $R^{10a}$ is $C_1$–$C_6$ lower alkyl or $C_3$–$C_6$ cycloalkyl, in the presence of a palladium catalyst and carbon monoxide to obtain the ester of the formula

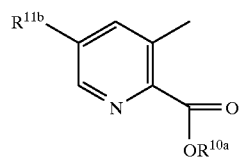

followed by reacting the ester with an amine of formula $NHR^{5a}R^{6a}$ to obtain the amide;

(b) reacting the amide with an iodo-substituted benzyl compound of the formula

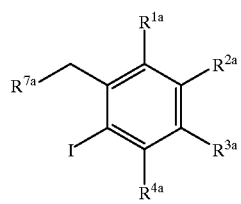

wherein $R^{1a}$, $R^{2a}$, $R^{3a}$, $R^{4a}$ and $R^{7a}$ are as defined above, in the presence of a strong base to obtain a compound of the formula

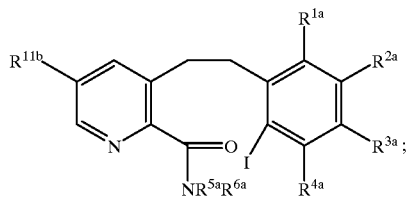

(c) cyclizing a compound of step (b) with a reagent of the formula $R^{8a}MgL$, wherein $R^{8a}$ is $C_1$–$C_8$ alkyl, aryl or heteroaryl and L is Br or Cl, provided that prior to cyclization, compounds wherein $R^{5a}$ or $R^{6a}$ is hydrogen are reacted with a- suitable N-protecting group.

(+)-Isomers of compounds of formula II wherein X is CH can be prepared with high enantioselectivity by using a process comprising enzyme catalyzed transesterification. Preferably, a racemic compound of formula II, wherein X is C, the double bond is present and $R^3$ is not H, is reacted with an enzyme such as Toyobo LIP-300 and an acylating agent such as trifluoroethly isobutyrate; the resultant (+)-amide is then hydrolyzed, for example by refluxing with an acid such as $H_2SO_4$, to obtain the corresponding optically enriched (+)-isomer wherein X is CH and $R^3$ is not H. Alternatively, a racemic compound of formula II, wherein X is C, the double bond is present and $R^3$ is not H, is first reduced to the corresponding racemic compound of formula II wherein X is CH and then treated with the enzyme (Toyobo LIP-300) and acylating agent as described above to obtain the (+)-amide, which is hydrolyzed to obtain the optically enriched (+)-isomer.

Compounds of formula III can be prepared from compounds of formula II by procedures known in the art, for example by reacting 1-N-t-butoxy-carbonylpiperidinyl-4-acetic acid with the compound of formula If under the standard amide coupling conditions described above.

The acids of formula HOOC—$(CH_2)_n$—$R^5$ or HOOC—$(CH_2)_{n3}$—$R^5$ $^a$re, wherein n, $n_3$ and $R^5$ $^a$re as defined above, are known in the art or can be prepared by method described in the literature.

Compounds useful in this invention are exemplified by the following preparative examples, which should not be construed to limit the scope of the disclosure. Alternative mechanistic pathways and analogous structures within the scope of the invention may be apparent to those skilled in the art.

PREPARATIVE EXAMPLE 1

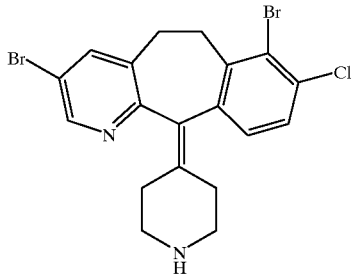

Step A:

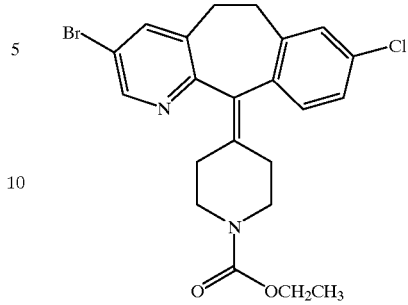

Combine 25.86 g (55.9 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 250 mL of concentrated $H_2SO_4$ at –5° C., then add 4.8 g (56.4 mmol) of $NaNO_3$ and stir for 2 hours. Pour the mixture into 600 g of ice and basify with concentrated $NH_4OH$ (aqueous). Filter the mixture, wash with 300 mL of water, then extract with 500 mL of $CH_2Cl_2$. Wash the extract with 200 mL of water, dry over $MgSO_4$, then filter and concentrate in vacuo to a residue. Chromatograph the residue (silica gel, 10% EtOAc/$CH_2Cl_2$) to give 24.4 g (86% yield) of the product. m.p.=165–167° C., Mass Spec.: $MH^+$=506, 508 (Cl). elemental analysis: calculated—C, 52.13; H, 4.17; N, 8.29 found—C, 52.18; H, 4.51; N, 8.16

Step B:

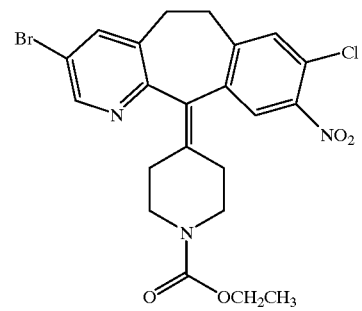

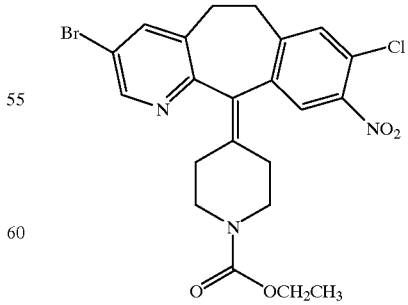

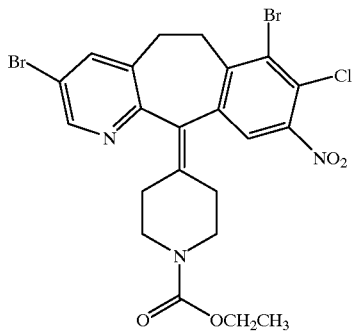

Combine 20 g (40.5 mmol) of the product of Step A and 200 mL of concentrated H₂SO₄ at 20° C., then cool the mixture to 0° C. Add 7.12 g (24.89 mmol) of 1,3-dibromo-5,5-dimethyl-hydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated NH₄OH (aqueous) at 0° C., and collect the resulting solid by filtration. Wash the solid with 300 mL of water, slurry in 200 mL of acetone and filter to provide 19.79 g (85.6% yield) of the product. m.p.=236–237° C., Mass Spec.: MH⁺=586 (Cl). elemental analysis: calculated—C, 45.11; H, 3.44; N, 7.17 found—C, 44.95; H, 3.57; N, 7.16

Step C:

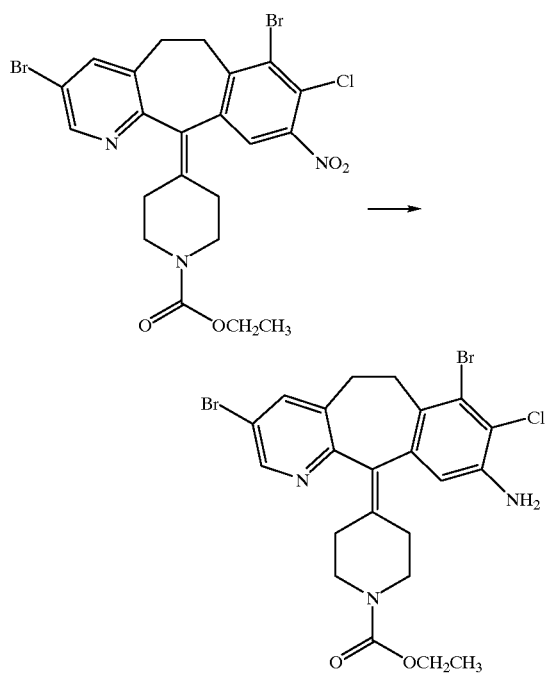

Combine 25 g (447 mmol) of Fe filings, 10 g (90 mmol) of CaCl₂ and a suspension of 20 g (34.19 mmol) of the product of Step B in 700 mL of 90:10 EtOH/water at 50° C. Heat the mixture at reflux overnight, filter through Celite® and wash the filter cake with 2×200 mL of hot EtOH. Combine the filtrate and washes, and concentrate in vacuo to a residue. Extract the residue with 600 mL of CH₂Cl₂, wash with 300 mL of water and dry over MgSO₄. Filter and concentrate in vacuo to a residue, then chromatograph (silica gel, 30% EtOAc/CH₂Cl₂) to give 11.4 g (60% yield) of the product. m.p.=211–212° C., Mass Spec.: MH⁺=556 (Cl). elemental analysis: calculated—C, 47.55; H, 3.99; N, 7.56 found—C, 47.45; H, 4.31; N, 7.49

Step D:

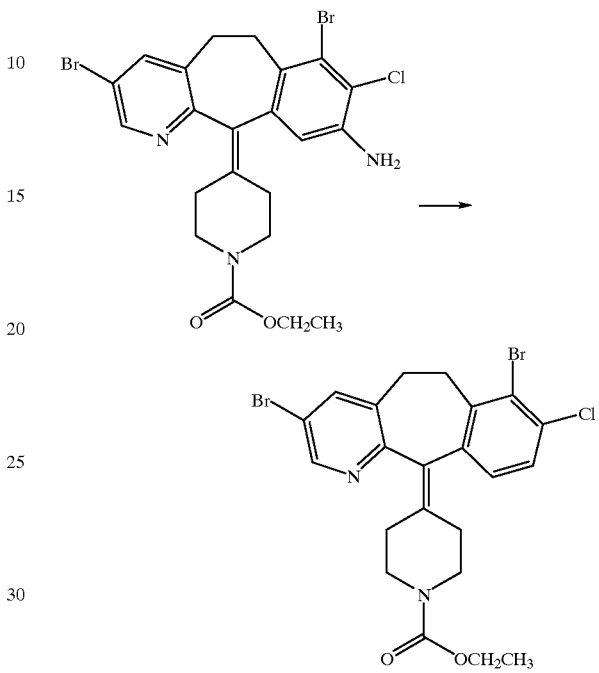

Slowly add (in portions) 20 g (35.9 mmol) of the product of Step C to a solution of 8 g (116 mmol) of NaNO₂ in 120 mL of concentrated HCl (aqueous) at −10° C. Stir the resulting mixture at 0° C. for 2 hours, then slowly add (dropwise) 150 mL (1.44 mole) of 50% H₃PO₂ at 0° C. over a 1 hour period. Stir at 0° C. for 3 hours, then pour into 600 g of ice and basify with concentrated NH₄OH (aqueous). Extract with 2×300 mL of CH₂Cl₂, dry the extracts over MgSO₄, then filter and concentrate in vacuo to a residue. Chromatograph the residue (silica gel, 25% EtOAc/hexanes) to give 13.67 g (70% yield) of the product. m.p.=163–165° C., Mass Spec.: MH⁺=541 (Cl). elemental analysis: calculated—C, 48.97; H, 4.05; N, 5.22 found—C, 48.86; H, 3.91; N, 5.18

Step E:

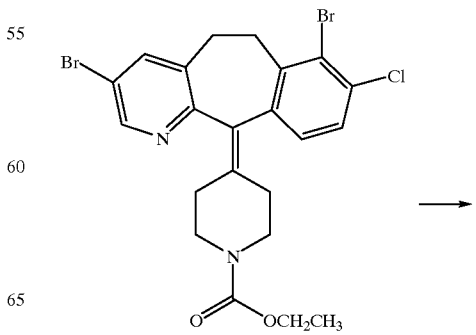

-continued

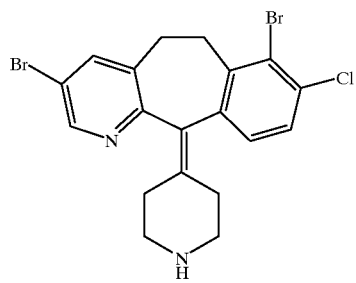

Combine 6.8 g (12.59 mmol) of the product of Step D and 100 mL of concentrated HCl (aqueous) and stir at 85° C. overnight. Cool the mixture, pour it into 300 g of ice and basify with concentrated NH₄OH (aqueous). Extract with 2×300 mL of CH₂Cl₂, then dry the extracts over MgSO₄. Filter, concentrate in vacuo to a residue, then chromatograph (silica gel, 10% MeOH/EtOAc+2% NH₄OH (aq.)) to give 5.4 g (92% yield) of the title compound. m.p.=172–174° C., Mass Spec.: MH⁺=469 (FAB). elemental analysis: calculated—C, 48.69; H, 3.65; N, 5.97 found—C, 48.83; H, 3.80; N, 5.97

PREPARATIVE EXAMPLE 2

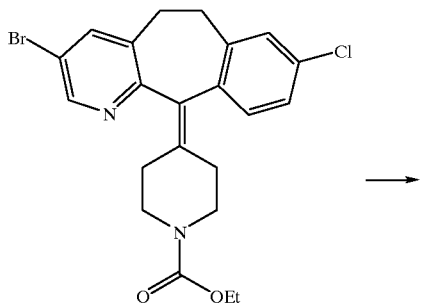

Step A:

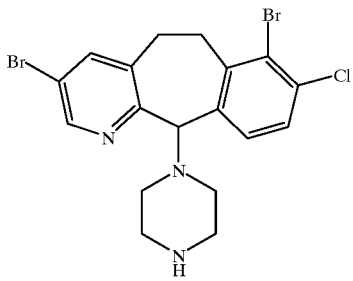

Hydrolyze 2.42 g of 4-(8-chloro-3-bromo-5,6-dihydro-11H-benzo[5,6]cyclohepta[1,2-b]pyridin-11-ylidene)-1- piperidine-1-carboxylic acid ethyl ester by dissolving in concentrated HCl and heating to about 100° C. for @ 16 hours. Cool the mixture, the neutralize with 1 M NaOH (aqueous). Extract with CH₂Cl₂, dry the extracts over MgSO₄, filter and concentrate in vacuo to give 1.39 g (69% yield) of the product.

Step B:

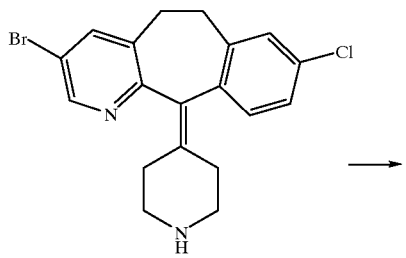

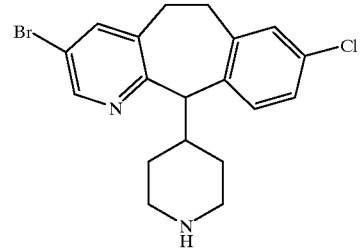

Combine 1 g (2.48 mmol) of the product of Step A and 25 mL of dry toluene, add 2.5 mL of 1 M DIBAL in toluene and heat the mixture at reflux. After 0.5 hours, add another 2.5 mL of 1 M DIBAL in toluene and heat at reflux for 1 hour. (The reaction is monitored by TLC using 50% MeOH/CH₂Cl₂+NH₄OH (aqueous).) Cool the mixture to room temperature, add 50 mL of 1 N HCl (aqueous) and stir for 5 min. Add 100 mL of 1 N NaOH (aqueous), then extract with EtOAc (3×150 mL). Dry the extracts over MgSO₄, filter and concentrate in vacuo to give 1.1 g of the title compound.

PREPARATIVE EXAMPLE 3

[racemic as well as (+)- and (-)- isomers]

Step A:

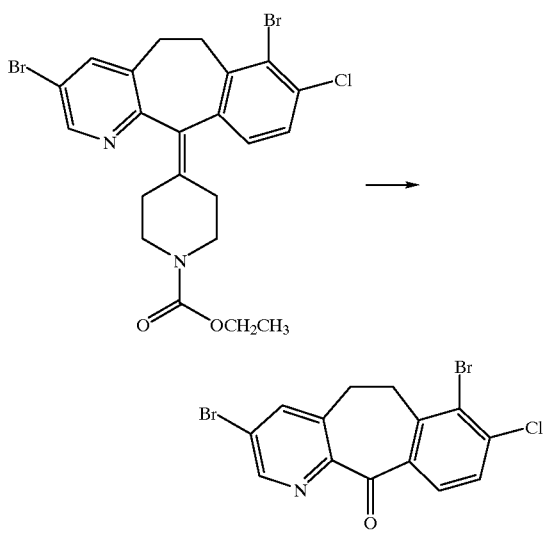

Combine 16.6 g (0.03 mole) of the product of Preparative Example 1, Step D, with a 3:1 solution of CH$_3$CN and water (212.65 mL CH$_3$CN and 70.8 mL of water) and stir the resulting slurry overnight at room temperature. Add 32.833 g (0.153 mole) of NaIO$_4$ and then 0.31 g (2.30 mmol) of RuO$_2$ and stir at room temperature give 1.39 g (69% yield) of the product. (The addition of RuO is accompanied by an exothermic reaction and the temperature climbs from 20° to 30° C.) Stir the mixture for 1.3 hrs. (temperature returned to 25° C. after about 30 min.), then filter to remove the solids and wash the solids with CH$_2$Cl$_2$. Concentrate the filtrate in vacuo to a residue and dissolve the residue in CH$_2$Cl$_2$. Filter to remove insoluble solids and wash the solids with CH$_2$Cl$_2$. Wash the filtrate with water, concentrate to a volume of about 200 mL and wash with bleach, then with water. Extract with 6 N HCl (aqueous). Cool the aqueous extract to 0° C. and slowly add 50% NaOH (aqueous) to adjust to pH=4 while keeping the temperature <30° C. Extract twice with CH$_2$Cl$_2$, dry over MgSO$_4$ and concentrate in vacuo to a residue. Slurry the residue in 20 mL of EtOH and cool to 0° C. Collect the resulting solids by filtration and dry the solids in vacuo to give 7.95 g of the product. $^1$H NMR (CDCl$_3$, 200 MHz): 8.7 (s, 1H); 7.85 (m, 6H); 7.5 (d, 2H); 3.45 (m, 2H); 3.15 (m, 2H).

Step B:

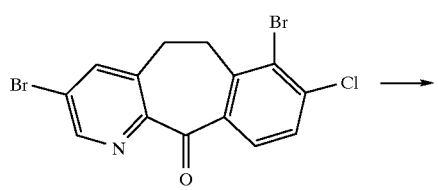

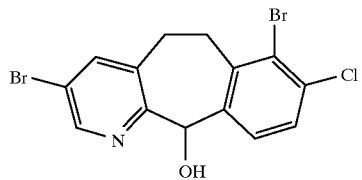

Combine 21.58 g (53.75 mmol) of the product of Step A and 500 mL of an anhydrous 1:1 mixture of EtOH and toluene, add 1.43 g (37.8 mmol) of NaBH$_4$ and heat the mixture at reflux for 10 min. Cool the mixture to 0° C., add 100 mL of water, then adjust to pH≈4–5 with 1 M HCl (aqueous) while keeping the temperature <10° C. Add 250 mL of EtOAc and separate the layers. Wash the organic layer with brine (3×50 mL) then dry over Na$_2$SO$_4$. Concentrate in vacuo to a residue (24.01 g) and chromatograph the residue (silica gel, 30% hexane/CH$_2$Cl$_2$) to give the product. Impure fractions were purified by rechromatography. A total of 18.57 g of the product was obtained. $^1$H NMR (DMSO-d$_6$, 400 MHz): 8.5 (s, 1H); 7.9 (s, 1H); 7.5 (d of d, 2H); 6.2 (s, 1H); 6.1 (s, 1H); 3.5 (m, 1H); 3.4 (m, 1H); 3.2 (m, 2H).

Step C:

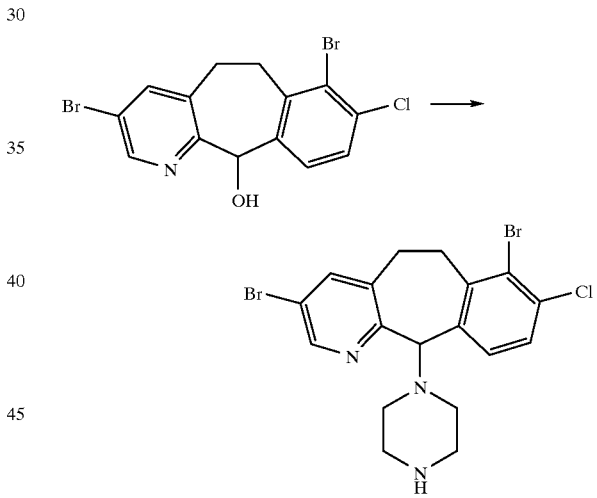

Combine 18.57 g (46.02 mmol) of the product of Step B and 500 mL of CHCl$_3$, then add 6.70 mL (91.2 mmol) of SOCl$_2$, and stir the mixture at room temperature for 4 hrs. Add a solution of 35.6 g (0.413 mole) of piperazine in 800 mL of THF over a period of 5 min. and stir the mixture for 1 hr. at room temperature. Heat the mixture at reflux overnight, then cool to room temperature and dilute the mixture with 1 L of CH$_2$Cl$_2$. Wash with water (5×200 mL), and extract the aqueous wash with CHCl$_3$ (3×100 mL). Combine all of the organic solutions, wash with brine (3×200 mL) and dry over MgSO$_4$. Concentrate in vacuo to a residue and chromatograph (silica gel, gradient of 5%, 7.5%, 10% MeOH/CH$_2$Cl$_2$+NH$_4$OH) to give 18.49 g of the title compound as a racemic mixture.

Step D—Separation of Enantiomers:

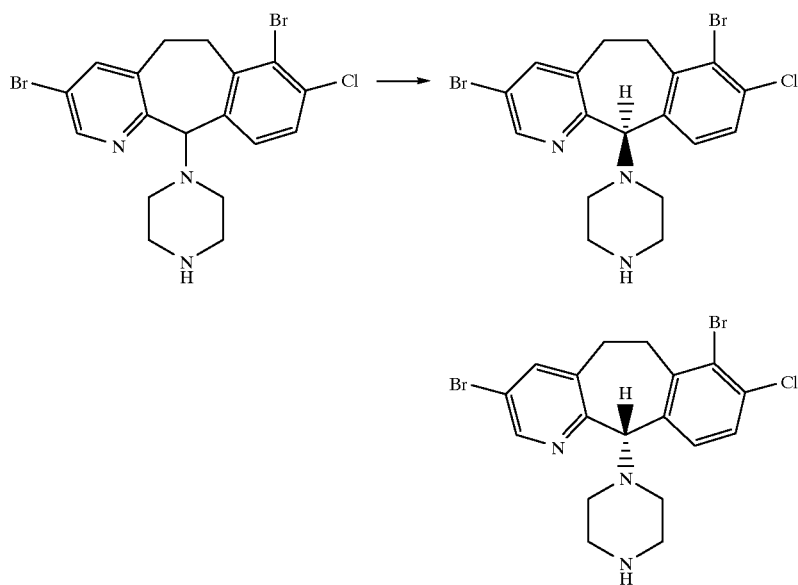

The racemic title compound of Step C is separated by preparative chiral chromatography (Chiralpack AD, 5 cm×50 cm column, flow rate 100 mL/min., 20% iPrOH/hexane+0.2% diethylamine), to give 9.14 g of the (+)-isomer and 9.30 g of the (−)-isomer.

Physical chemical data for (+)-isomer: m.p.=74.5°–77.5° C.; Mass Spec. MH$^+$=471.9; $[a]_D^{25}$=+97.4° (8.48 mg/2mL MeOH).

Physical chemical data for (−)-isomer: m.p.=82.9°–84.5° C.; Mass Spec. MH$^+$=471.8; $[a]_D^{25}$=−97.4° (8.32 mg/2mL MeOH).

PREPARATIVE EXAMPLE 4

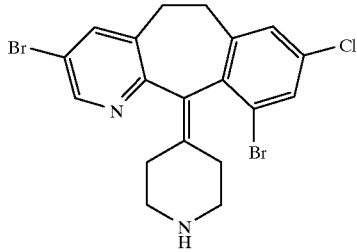

Step A:

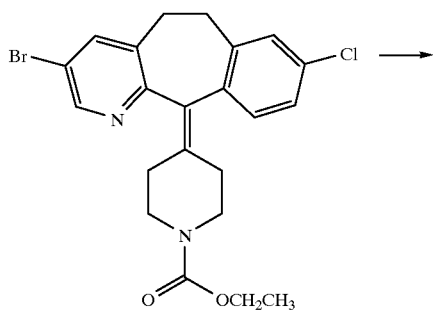

-continued

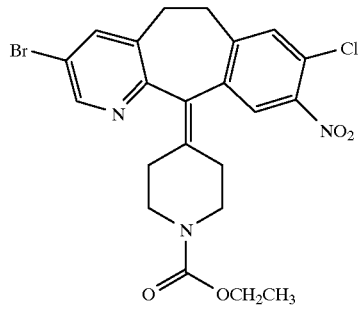

Combine 15 g (38.5 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 150 mL of conc. H$_2$SO$_4$ at −5° C., then add 3.89 g (38.5 mmol) of KNO$_3$ and stir for 4 h. Pour the mixture into 3 L of ice and basify with 50% NaOH (aqueous). Extract with CH$_2$Cl$_2$, dry over MgSO$_4$, then filter and concentrate in vacuo to a residue. Recrystallize the residue from acetone to give 6.69 g of the product. $^1$H NMR (CDCl$_3$, 200 MHz): 8.5 (s, 1H); 7.75 (s, 1H); 7.6 (s, 1H); 7.35 (s, 1H); 4.15 (q, 2H); 3.8 (m, 2H); 3.5–3.1 (m, 4H); 3.0–2.8 (m, 2H); 2.6–2.2 (m, 4H); 1.25 (t, 3H).

Step B:

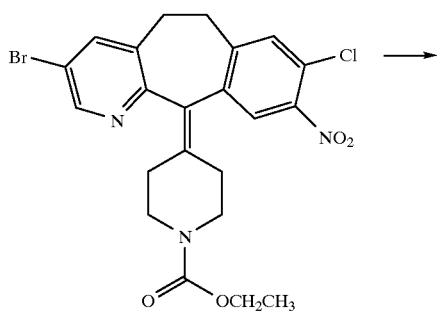

Combine 6.69 g (13.1 mmol) of the product of Step A and 100 mL of 85% EtOH/water, add 0.66 g (5.9 mmol) of CaCl$_2$ and 6.56 g (117.9 mmol) of Fe and heat the mixture at reflux overnight. Filter the hot reaction mixture through celite® and rinse the filter cake with hot EtOH. Concentrate the filtrate in vacuo to give 7.72 g of the product. Mass Spec.: MH$^+$=478.0

Step C:

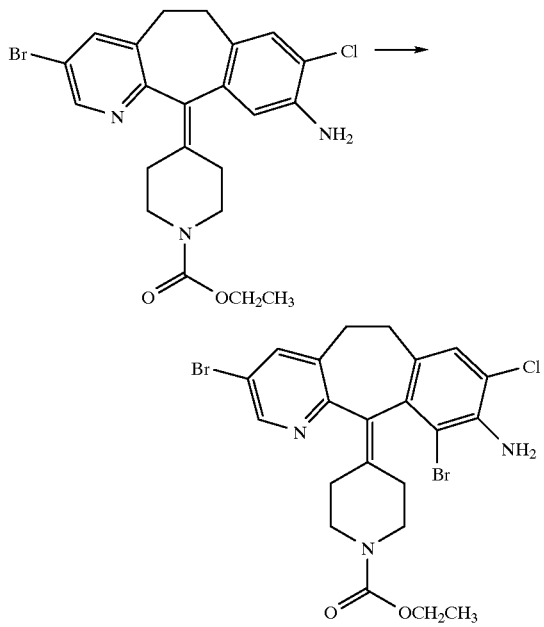

Combine 7.70 g of the product of Step B and 35 mL of HOAc, then add 45 mL of a solution of Br$_2$ in HOAc and stir the mixture at room temperature overnight. Add 300 mL of 1 N NaOH (aqueous), then 75 mL of 50% NaOH (aqueous) and extract with EtOAc. Dry the extract over MgSO$_4$ and concentrate in vacuo to a residue. Chromatograph the residue (silica gel, 20%–30% EtOAc/hexane) to give 3.47 g of the product (along with another 1.28 g of partially purified product).

Mass Spec.: MH$^+$=555.9. $^1$H NMR (CDCl$_3$, 300 MHz): 8.5 (s, 1H); 7.5 (s, 1H); 7.15 (s, 1H); 4.5 (s, 2H); 4.15 (m, 3H); 3.8 (brs, 2H); 3.4–3.1 (m, 4H); 9–2.75 (m, 1H); 2.7–2.5 (m, 2H); 2.4–2.2 (m, 2H); 1.25 (m, 3H).

Step D:

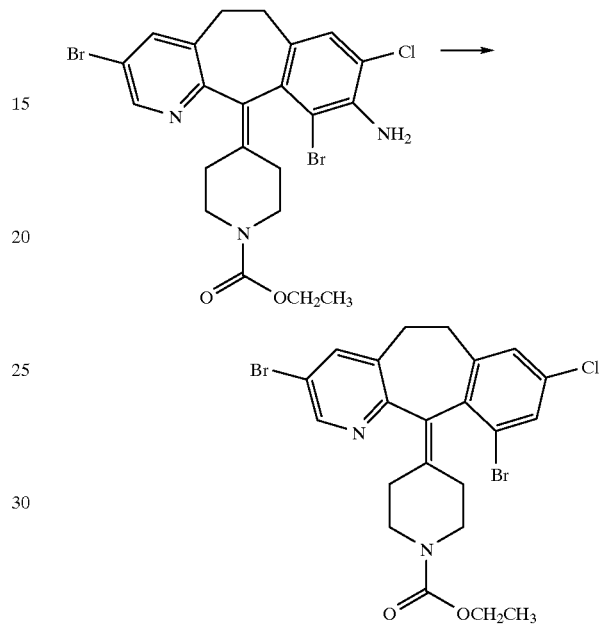

Combine 0.557 g (5.4 mmol) of t-butylnitrite and 3 mL of DMF, and heat the mixture at to 60°–70° C. Slowly add (dropwise) a mixture of 2.00 g (3.6 mmol) of the product of Step C and 4 mL of DMF, then cool the mixture to room temperature. Add another 0.64 mL of t-butylnitrite at 40° C. and reheat the mixture to 60°–70° C. for 0.5 hrs. Cool to room temperature and pour the mixture into 150 mL of water. Extract with CH$_2$Cl$_2$, dry over MgSO$_4$ and concentrate in vacuo to a residue. Chromatograph the residue (silica gel, 10%–20% EtOAc/hexane) to give 0.74 g of the product.

Mass Spec.: MH$^+$=541.0. $^1$H NMR (CDCl3, 200 MHz): 8.52 (s, 1H); 7.5 (d, 2H); 7.2 (s, 1H); 4.15 (q, 2H); 3.9–3.7 (m, 2H); 3.5–3.1 (m, 4H); 3.0–2.5 (m, 2H); 2.4–2.2 (m, 2H); 2.1–1.9 (m, 2H); 1.26 (t, 3H).

Step E:

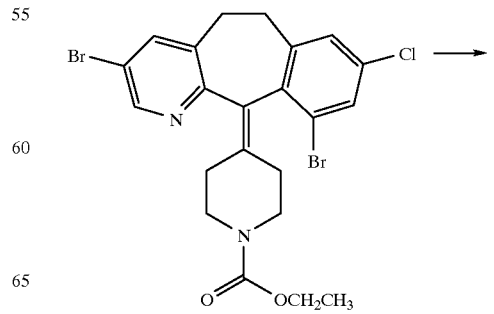

-continued

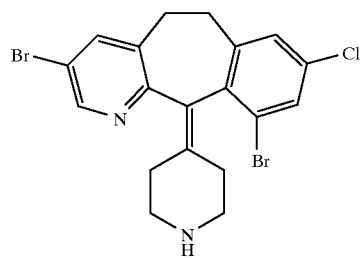

Combine 0.70 g (1.4 mmol) of the product of Step D and 8 mL of concentrated HCl (aqueous) and heat the mixture at reflux overnight. Add 30 mL of 1 N NaOH (aqueous), then 5 mL of 50% NaOH (aqueous) and extract with $CH_2Cl_2$. Dry the extract over $MgSO_4$ and concentrate in vacuo to give 0.59 g of the title compound. Mass Spec.: $M^+$468.7. m.p.= 123.9°–124.2° C.

PREPARATIVE EXAMPLE 5

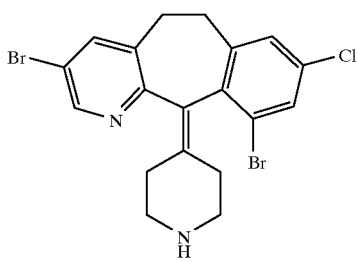

[racemic as well as (+)- and (-)-isomers]

Step A:

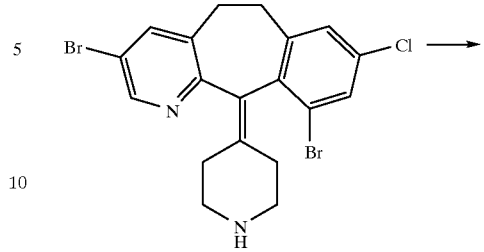

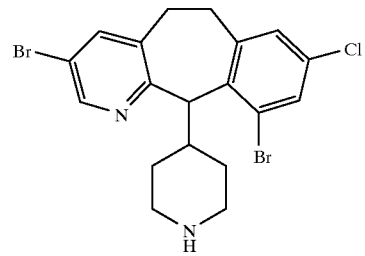

Prepare a solution of 8.1 g of the title compound from Preparative Example 4 in toluene and add 17.3 mL of a 1M solution of DIBAL in toluene. Heat the mixture at reflux and slowly add (dropwise) another 21 mL of 1M DIBAL/toluene solution over a period of 40 min. Cool the reaction mixture to about 0° C. and add 700 mL of 1 M HCl (aqueous). Separate and discard the organic phase. Wash the aqueous phase with $CH_2Cl_2$, discard the extract, then basify the aqueous phase by adding 50% NaOH (aqueous). Extract with $CH_2Cl_2$, dry the extract over $MgSO_4$ and concentrate in vacuo to give 7.30 g of the title compound, which is a racemic mixture of enantiomers.

Step B—Separation of Enantiomers:

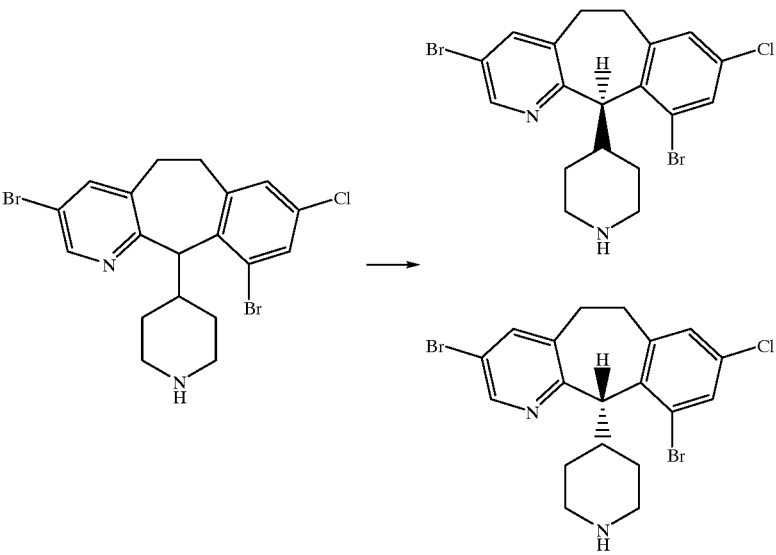

The racemic title compound of Step A is separated by preparative chiral chromatography (Chiralpack AD, 5 cm×50 cm column, using 20% iPrOH/hexane+0.2% diethylamine), to give the (+)-isomer and the (−)-isomer of the title compound.

Physical chemical data for (+)-isomer: m.p.=148.8° C.; Mass Spec. MH$^+$=469; $[a]_D^{25}$=+65.6° (mg/2mL MeOH).

Physical chemical data for (−)-isomer: m.p.=112° C.; Mass Spec. MH$^+$=469; $[a]_D^{25}$=−65.2° (mg/2mL MeOH).

PREPARATIVE EXAMPLE 6

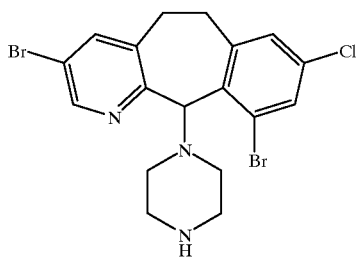

[racemic as well as (+)- and (−)-isomers]

Step A:

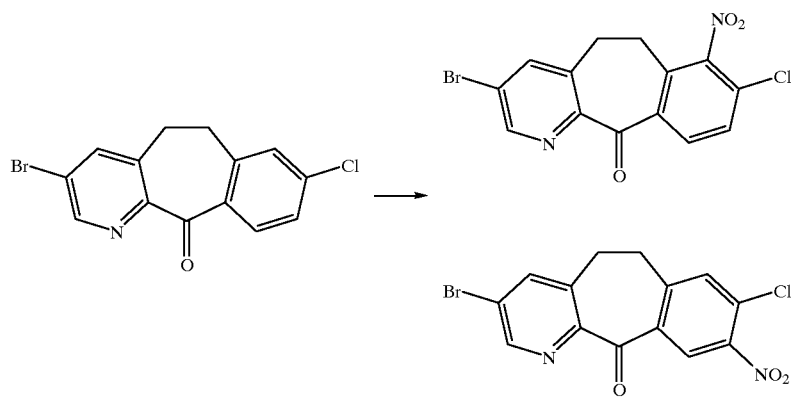

Combine 40.0 g (0.124 mole) of the starting ketone and 200 mL of $H_2SO_4$ and cool to 0° C. Slowly add 13.78 g (0.136 mole) of $KNO_3$ over a period of 1.5 hrs., then warm to room temperature and stir overnight. Work up the reaction using substantially the same procedure as described for Preparative Example 1, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro compounds.

Step B:

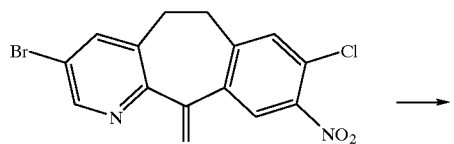

-continued

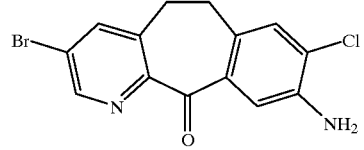

React 28 g (76.2 mmol) of the 9-nitro product of Step A, 400 mL of 85% EtOH/water, 3.8 g (34.3 mmol) of $CaCl_2$ and 38.28 g (0.685 mole) of Fe using substantially the same procedure as described for Preparative Example 1, Step C, to give 24 g of the product Step C:

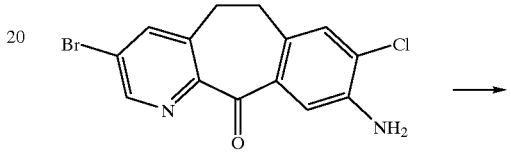

-continued

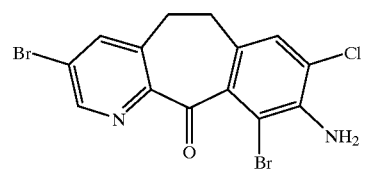

Combine 13 g (38.5 mmol) of the product of Step B, 140 mL of HOAc and slowly add a solution of 2.95 mL (57.8 mmol) of $Br_2$ in 10 mL of HOAc over a period of 20 min. Stir the reaction mixture at room temperature, then concentrate in vacuo to a residue. Add $CH_2Cl_2$ and water, then adjust to pH=8–9 with 50% NaOH (aqueous). Wash the organic phase with water, then brine and dry over $Na_2SO_4$. Concentrate in vacuo to give 11.3 g of the product.

Step D:

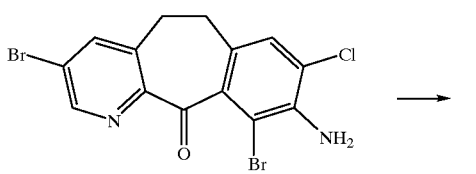

Cool 100 mL of concentrated HCl (aqueous) to 0° C., then add 5.61 g (81.4 mmol) of $NaNO_2$ and stir for 10 min. Slowly add (in portions) 11.3 g (27.1 mmol) of the product of Step C and stir the mixture at 0°–30° C. for 2.25 hrs. Slowly add (dropwise) 180 mL of 50% $H_3PO_2$ (aqueous) and allow the mixture to stand at 0° C. overnight. Slowly add (dropwise) 150 mL of 50% NaOH over 30 min., to adjust to pH=9, then extract with $CH_2Cl_2$. Wash the extract with water, then brine and dry over $Na_2SO4$. Concentrate in vacuo to a residue and chromatograph (silica gel, 2% $EtOAc/CH_2Cl_2$) to give 8.6 g of the product.

Step E:

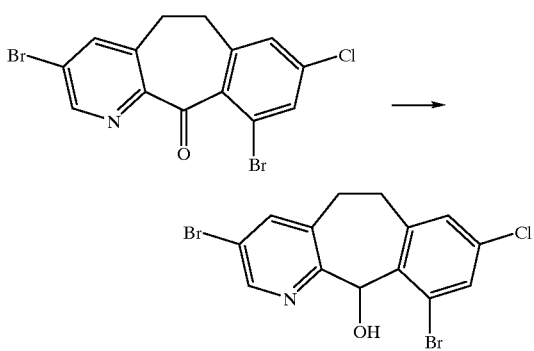

Combine 8.6 g (21.4 mmol) of the product of Step D and 300 mL of MeOH and cool to 0°–2° C. Add 1.21 g (32.1 mmol) of $NaBH_4$ and stir at ~0° C. for 1 hr. Add another 0.121 g (3.21 mmol) of $NaBH_4$, stir for 2 hr. at 0° C., then let stand overnight at 0° C. Concentrate in vacuo to a residue then partition the residue between $CH_2Cl_2$ and water. Separate the organic phase and concentrate in vacua (50° C.) to give 8.2 g of the product.

Step F:

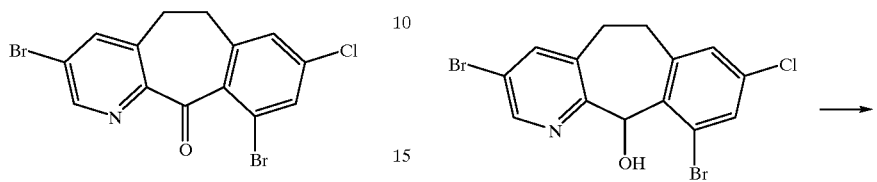

Combine 8.2 g (20.3 mmol) of the product of Step E and 160 mL of $CH_2Cl_2$, cool to 0° C., then slowly add (dropwise) 14.8 mL (203 mmol) of $SOCl_2$ over a 30 min. period. Warm the mixture to room temperature and stir for 4.5 hrs., then concentrate in vacuo to a residue, add $CH_2Cl_2$ and wash with 1 N NaOH (aqueous) then brine and dry over $Na_2SO_4$. Concentrate in vacuo to a residue, then add dry THF and 8.7 g (101 mmol) of piperazine and stir at room temperature overnight. Concentrate in vacuo to a residue, add $CH_2Cl_2$, and wash with 0.25 N NaOH (aqueous), water, then brine. Dry over $Na_2SO_4$ and concentrate in vacuo to give 9.46 g of the crude product. Chromatograph (silica gel, 5% MeOH/$CH_2Cl_2+NH_3$) to give 3.59 g of the title compound, as a racemate. $^1H$ NMR ($CDCl_3$, 200 MHz): 8.43 (d, 1H); 7.55 (d, 1H); 7.45 (d, 1H); 7.11 (d, 1H); 5.31 (s, 1H); 4.86–4.65 (m, 1H); 3.57–3.40 (m, 1H); 2.98–2.55 (m, 6H); 2.45–2.20 (m, 5H).

Step G—Separation of Enantiomers:

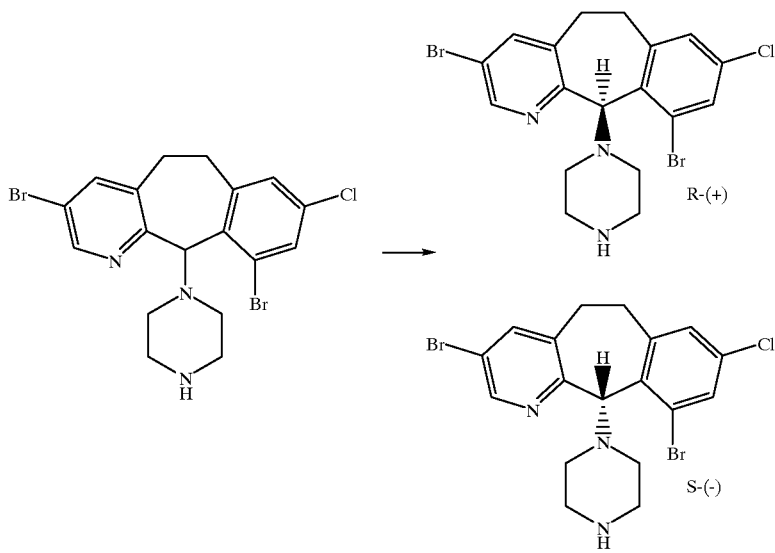

The racemic title compound from Step F (5.7 g) is chromatographed as described for Preparative Example 3, Step D, using 30% iPrOH/hexane +0.2% diethylamine, to give 2.88 g of the R-(+)-isomer and 2.77 g of the S-(-)-isomer of the title compound.

Physical chemical data for the R-(+)-isomer: Mass Spec. $MH^+$=470; $[a]_D^{25}$=+12.1° (10.9 mg/2mL MeOH).

Physical chemical data for the S-(-)-isomer: Mass Spec. $MH^+$=470; $[a]_D^{25}$=-13.2° (11.51 mg/2mL MeOH).

PREPARATIVE EXAMPLE 7

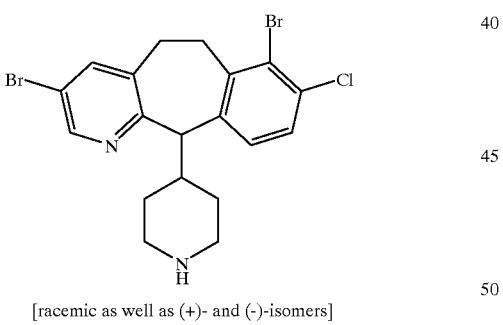

[racemic as well as (+)- and (-)-isomers]

Step A:

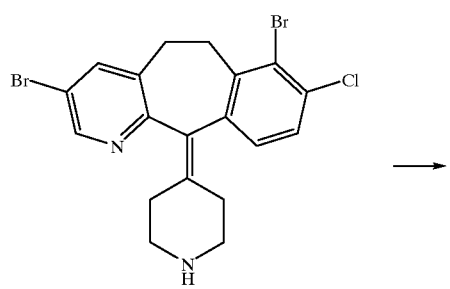

-continued

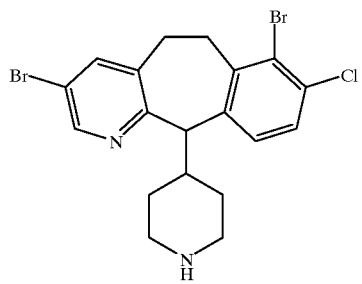

Combine 13 g (33.3 mmol) of the title compound from Preparative Example 1, Step D, and 300 mL of toluene at 20° C., then add 32.5 mL (32.5 mmol) of a 1 M solution of DIBAL in toluene. Heat the mixture at reflux for 1 hr., cool to 20° C., add another 32.5 mL of 1 M DIBAL solution and heat at reflux for 1 hr. Cool the mixture to 20° C. and pour it into a mixture of 400 g of ice, 500 mL of EtOAc and 300 mL of 10% NaOH (aqueous). Extract the aqueous layer with $CH_2Cl_2$ (3×200 mL), dry the organic layers over $MgSO_4$, then concentrate in vacuo to a residue. Chromatograph (silica gel, 12% $MeOH/CH_2Cl_2$+4% $NH_4OH$) to give 10.4 g of the title compound as a racemate. Mass Spec.: $MH^+$=469 (FAB). partial $^1H$ NMR ($CDCl_3$, 400 MHz): 8.38 (s, 1H); 7.57 (s, 1H); 7.27 (d, 1H); 7.06 (d, 1H); 3.95 (d, 1H).

Step B—Separation of Enantiomers:

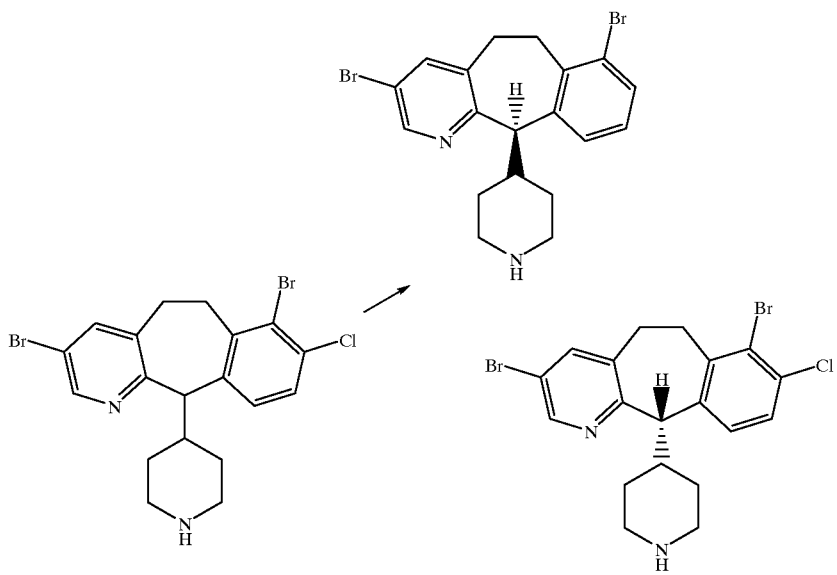

The racemic title compound of Step A is separated by preparative chiral chromatography (Chiralpack AD, 5 cm×50 cm column, using 5% iPrOH/hexane+0.2% diethylamine), to give the (+)-isomer and the (−)-isomer of the title compound.

Physical chemical data for (+)-isomer: Mass Spec. MH$^+$= 470.9 (FAB); $[a]_D^{25}$=+43.5° (c=0.402, EtOH); partial $^1$H NMR (CDCl$_3$, 400 MHz): 8.38 (s, 1H); 7.57 (s, 1H); 7.27 (d, 1H); 7.05 (d, 1H); 3.95 (d, 1H).

Physical chemical data for (−)-isomer: Mass Spec. MH$^+$= 470.9 (FAB); $[a]_D^{25}$=−41.8° (c=0.328 EtOH); partial $^1$H NMR (CDCl$_3$, 400 MHz): 8.38 (s, 1H); 7.57 (s, 1H); 7.27 (d, 1H); 7.05 (d, 1H); 3.95 (d, 1H).

PREPARATIVE EXAMPLE 8

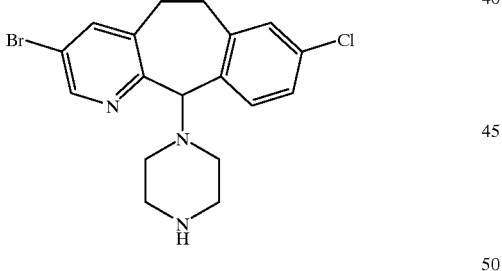

[racemic as well as R-(+)- and S-(−)-isomers]

Treat 4-(8-chloro-3-bromo-5,6-dihydro-11H-benzo[5,6]cyclohepta-[1,2-b]pyridin-11-ylidene)-1-piperidine-1-carboxylic acid ethyl ester via substantially the same procedure as described in Preparative Example 3, Steps A–D, to give as the product of Step C, the racemic title compound, and as the products of Step D the R-(+)-isomer and S-(−)-isomer of the title compound.

Physical chemical data for the R-(+)-isomer: $^{13}$C NMR (CDCl$_3$): 155.8 (C); 146.4 (CH); 140.5 (CH); 140.2 (C); 136.2 (C); 135.3 (C); 133.4 (C); 132.0 (CH); 129.9 (CH); 125.6 (CH); 119.3 (C); 79.1 (CH); 52.3 (CH$_2$); 52.3 (CH); 45.6 (CH$_2$); 45.6 (CH$_2$); 30.0 (CH$_2$); 29.8 (CH$_2$). $[a]_D^{25}$=+25.8° (8.46 mg/2 mL MeOH).

Physical chemical data for the S-(−)-isomer: $^{13}$C NMR (CDCl$_3$): 155.9 (C); 146.4 (CH); 140.5 (CH); 140.2 (C); 136.2 (C); 135.3 (C); 133.3 (C); 132.0 (CH); 129.9 (CH); 125.5 (CH); 119.2 (C); 79.1 (CH); 52.5 (CH$_2$); 52.5 (CH); 45.7 (CH$_2$); 45.7 (CH$_2$); 30.0 (CH$_2$); 29.8 (CH$_2$). $[a]_D^{25}$=−27.9° (8.90 mg/2 mL MeOH).

PREPARATIVE EXAMPLE 9

PREPARATIVE EXAMPLE 9

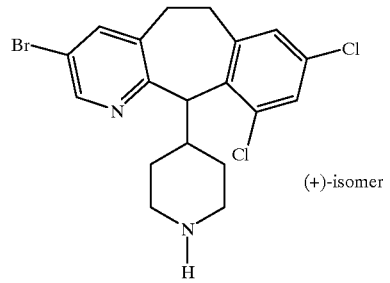

(+)-isomer

Step A:

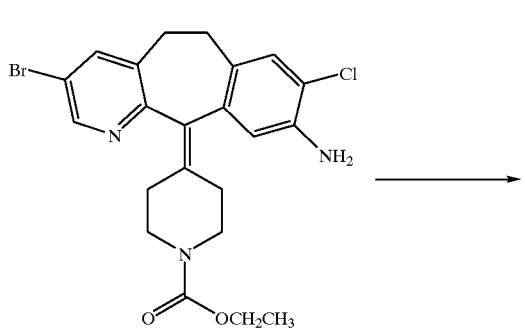

-continued

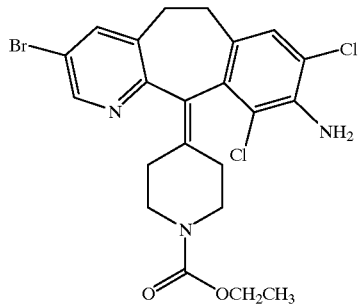

Dissolve 9.90 g (18.9 mmol) of the product of Preparative Example 4, Step B, in 150 mL CH$_2$Cl$_2$ and 200 mL of CH$_3$CN and heat to 60° C. Add 2.77 g (20.8 mmol) N-chlorosuccinimide and heat to reflux for 3 h., monitoring the reaction by TCL (30%EtOAc/H$_2$O). Add an additional 2.35 g (10.4 mmol) of N-chlorosuccinimide and reflux an additional 45 min. Cool the reaction mixture to room temperature and extract with 1 N NaOH and CH$_2$Cl$_2$. Dry the CH$_2$Cl$_2$ layer over MgSO$_4$, filter and purify by flash chromatography (1200 mL normal phase silica gel, eluting with 30% EtOAc/H$_2$O) to obtain 6.24 g of the desired product. M.p. 193–195.4° C.

Step B:

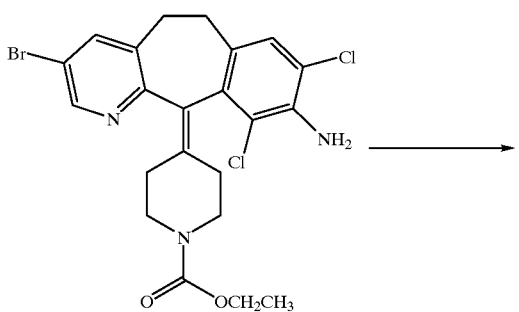

To 160 mL of conc. HCl at −10° C. add 2.07 g (30.1 mmol) NaNO$_2$ and stir for 10 min. Add 5.18 g (10.1 mmol) of the product of Step A and warm the reaction mixture from −10° C. to 0° C. for 2 h. Cool the reaction to −10° C., add 100 mL H$_3$PO$_2$ and let stand overnight. To extract the reaction mixture, pour over crushed ice and basifiy with 50% NaOH/CH$_2$Cl$_2$. Dry the organic layer over MgSO$_4$, filter and concentrate to dryness. Purify by flash chromatography (600 mL normal phase silica gel, eluting with 20% EtOAc/hexane) to obtain 3.98 g of product. Mass spec.: MH$^+$= 497.2.

Step C:

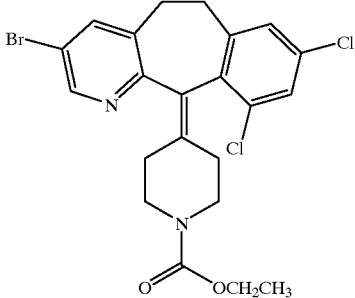

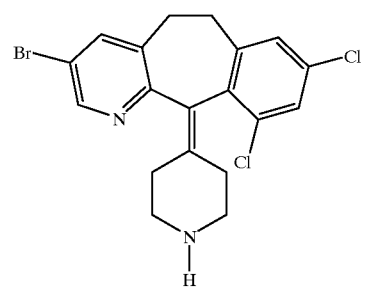

Dissolve 3.9 g of the product of Step B in 100 mL conc. HCl and reflux overnight. Cool the mixture, basify with 50% w/w NaOH and extract the resultant mixture with CH$_2$Cl$_2$. Dry the CH$_2$Cl$_2$ layer over MgSO$_4$, evaporate the solvent and dry under vacuum to obtain 3.09 g of the desired product. Mass spec.: MH$^+$=424.9.

Step D:

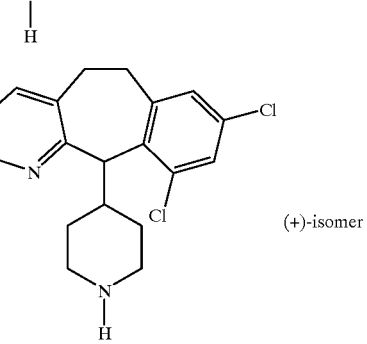

(+)-isomer

Using a procedure similar to that described in Preparative Example 5, obtain 1.73 g of the desired product, m.p. 169.6–170.1° C.; [a]$_D^{25}$=+48.2° (c=1, MeOH).

PREPARATIVE EXAMPLE 10

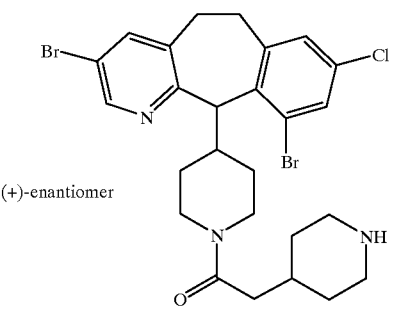
(+)-enantiomer

Step A:

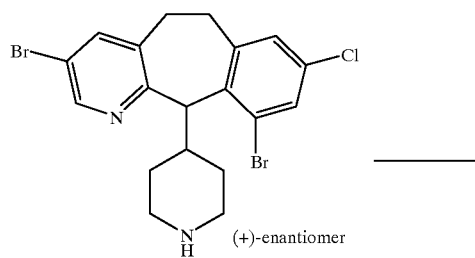
(+)-enantiomer

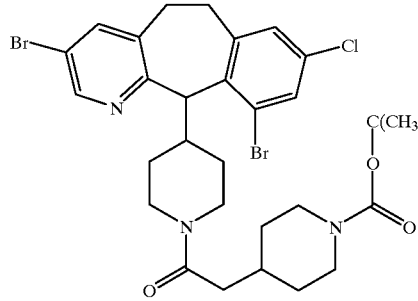

Combine 1.33 g of the (+)-enantiomer of the compound of Preparative Example 5, Step B, in anhydrous DMF with 1.37 g of 1-N-t-butoxy-carbonylpiperidinyl-4-acetic acid, and with DEC, HOBT and N-methylmorpholine. Stir the mixture at room temperature overnight.

Concentrate in vacuo to remove the DMF and add 50 mL of saturated $NaHCO_3$ (aqueous). Extract with $CH_2Cl_2$ (2×250 mL), wash the extracts with 50 mL of brine and dry over $MgSO_4$. Concentrate in vacuo to a residue and chromatograph (silica gel, 2% $CH_3OH/CH_2Cl_2$+10% $NH_4OH$) to give 2.78 g of the product. Mass Spec.: MH$^+$=694.0 (FAB); $[\alpha]_D^{25}$=+34.1° (5.45 mg/2 mL, MeOH).

Step B:

Combine 2.78 g of the product of Step A and $CH_2Cl_2$, then cool to 0° C. and add TFA. Stir the mixture for 3 h at 0° C., then add 1 N NaOH (aqueous) followed by 50% NaOH (aqueous). Extract with $CH_2Cl_2$, dry over $MgSO_4$ and concentrate in vacuo to give 1.72 g of the product. M.p.= 104.1° C.; Mass Spec.: MH$^+$=594; $[\alpha]_D^{25}$=+53.4° (11.42 mg/2 mL, $CH_3OH$).

EXAMPLE 1

4-(3-Bromo-8,10-dichloro-6,11-dihydro-5H-benzo[5,6]cyclohepta[1,2-b]pyridin-11-yl)-1-[(tetrahydro-2-oxo-2H-1 3-oxazin-5-yl)acetyl]piperidine

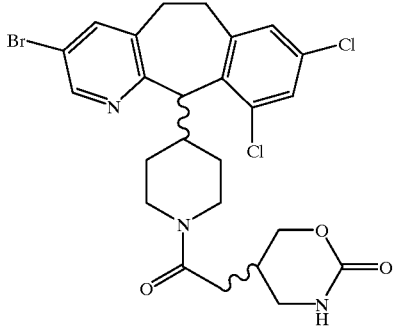

Step 1: 1,1-Dimethylethyl-3-[2-[4-(3-bromo-8,10-dichloro-6,11-dihydro-5H-benzo[5,6]cyclohepta[1,2-b]pyridin-11-yl)-1-piperidinyl]-2-oxoethyl]-1-azetidinecarboxylate

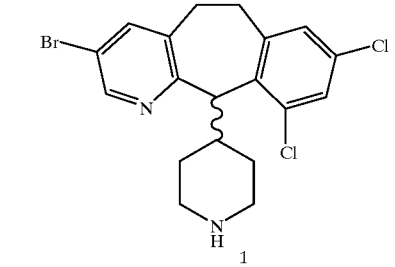

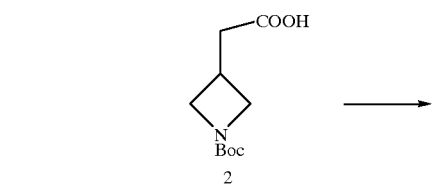

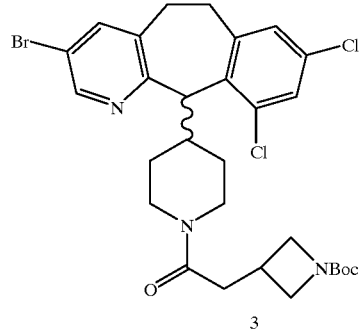

Dissolve 1.06 g (2.48 mmol) of the product of Preparative Example 9 (1) in 20 ml of DMF, stir at room temperature, and add 0.84 g (8.3 mmol) of 4-methylmorpholine, 0.48g (2.5 mmol) of DEC, 0.34 g (2.51 mmol) of HOBT, and 0.36 g (1.67 mmole)of 1-N-t-butoxycarbonylazetidinyl-3-acetic acid (2, prepared as described in *J. Chem. Research* (S) 1996, 430–431). Stir the mixture at room temperature for 2 days, concentrate in vacuo to a residue, then partition the residue between $CH_2Cl_2$ and water. Wash the organic phase successively with saturated $NaHCO_3$ (aqueous) and brine. Dry the organic phase over $MgSO_4$ and concentrate in vacuo to a residue. Chromatograph the residue (silica gel, 2%

CH₃OH/CH₂Cl₂+NH₃) to give 0.843 g of the title compound. Mass Spec.: MH⁺624; partial ¹H NMR (CDCl₃, 200 MHz): 8.48(d, 1H); 7.55 (s, 1H); 7.31 (d, 1H); 7.10 (s, 1H); 4.90 (d, 1H); 4.52 (d, 1H), 1.45 (s, 9H).

Step 2:

Combine 0.5g of the product 3 and 6 mL of CH₃CN, and add 0.175 g (0.32 mmole) of (Ce(NH₄)₂(NO₃)₆. Reflux the mixture for 2 h., then concentrate in vacuo to a residue. Extract with CH₂Cl₂, dry over MgSO₄ and concentrate in vacuo to give a residue. Chromatograph the residue (silica gel, 2% CH₃OH/CH₂Cl₂+NH₃) to give 0.165 g of the title compound. Mass Spec.: MH⁺568; partial ¹H NMR (CDCl₃, 200 MHz): 8.48 (d, 1H); 7.60 (s, 1H); 7.31 (d, 1H); 7.12 (s, 1H); 4.90 (d, 1H); 4.60 (d, 1H).

EXAMPLE 2

4-(3,10-Dibromo-8-chloro-6,11-dihydro-5H-benzo[5,6]cyclohepta[1,2-b]pyridin-11-yl)-1-[(tetrahydro-2-oxo-2H-1,3-oxazin-5-yl)acetyl]piperidine

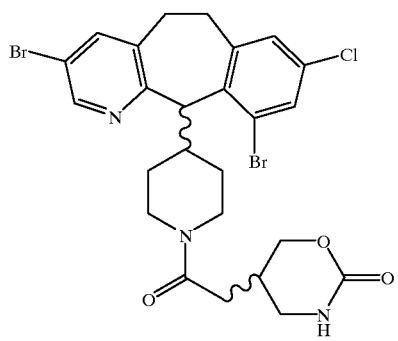

Step 1: 11-Dimethylethyl-3-[2-[4-(3-10-dibromo-8-chloro-6,11-dihydro-5H-benzo[5,6]cyclohepta[12-b]pyridin-11-yl)-1-piperidinyl]-2-oxoethyl]-1-azetidinecarboxylate.

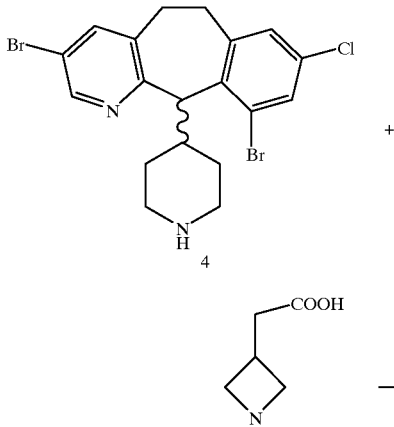

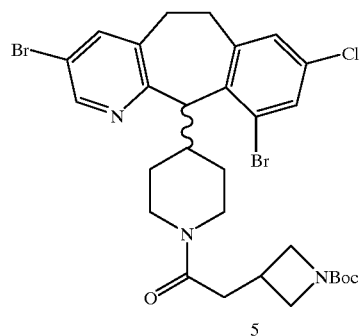

Using the procedure of Example 1, Step 1, but replacing 1 with the product of Preparative Example 5 (4), prepare compound 5. Mass Spec.: MH⁺668.88; partial ¹H NMR (CDCl₃, 200 MHz): 8.50 (d, 1H); 7.52 (s, 1H); 7.31 (d, 1H); 7.12 (s, 1H); 4.91 (d, 1H); 4.54 (d, 1H), 1.50 (s, 9H).

Step 2:

Combine 0.5 g, (0.747 mmole) of the product 5 and 10 mL of CH₃CN, and add 0.41 g (0.747 mmole) of (Ce(NH₄)₂(NO₃)₆. Reflux the mixture for 2 h., then concentrate in vacuo to a residue. Extract with CH₂Cl₂, dry over MgSO₄ and concentrate in vacuo to give a residue. Chromatograph the residue (silica gel, 2% CH₃OH/CH₂Cl₂+NH₃) to give 0.165 g of the title compound. Mass Spec.: MH⁺612; partial ¹H NMR (CDCl₃, 200 MHz): 8.42 (d, 1H); 7.52 (d 1H); 7.50 (d, 1H); 7.12 (d, 1H); 4.90 (d, 1H); 4.55 (d, 1H).

EXAMPLE 3

(+)-4[2-[4-(3,10-Dibromo-8-chloro-6,11-dihydro-5H-benzo[5.6]cyclohepta[1,2-b]pyridin-11(R)-yl-1-piperidinyl]-2-oxoethyl]-1-[(2-oxo-4(S)-oxazolidinyl)carbonyl]piperidine

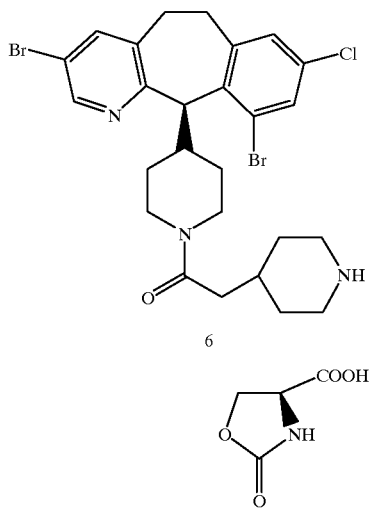

39
-continued

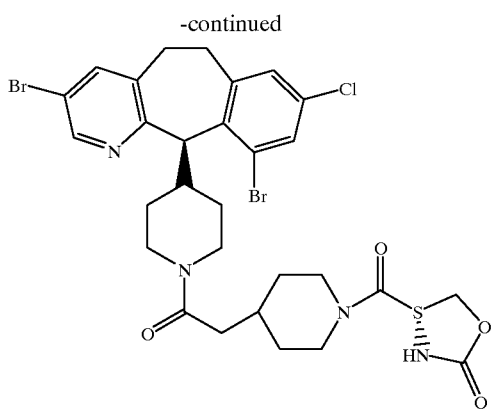

Dissolve 0.133 g (0.2187 mmol) of the product of Preparative Example 10 in 1.3 ml of DMF, stir at room temperature overnight, and add 0.069 g (0.68 mmol) of 4-methylmorpholine, 0.0565 g (0.293 mmol) of DEC, 0.0419 g (0.31 mmol) of HOBT, and 0.0386 g of 2-oxo-4 (S)-oxazolidine temperature for 2 days, then concentrate in vacuo to a residue and partition the residue between $CH_2Cl_2$ and water. Wash the organic phase successively with saturated $NaHCO_3$ (aqueous) and brine. Dry the organic phase over $MgSO_4$ and concentrate in vacuo to a residue. Thick layer chromatography of the residue (silica gel, 10% $CH_3OH/CH_2Cl_2+NH_3$) gives 0.123 g of the title compound. Mass Spec.: $MH^+707$; m.p.=155–166.6° C.

EXAMPLE 4

(+)-4[2-[4-(3,10-Dibromo-8-chloro-6,11-dihydro-5H-benzo[5,6]cyclohepta[1,2-b]pyridin-11(R)-yl-1-piperidinyl]-2-oxoethyl]-1-[(2-oxo-4(S)-imidazolidinyl)carbonyl]piperidine

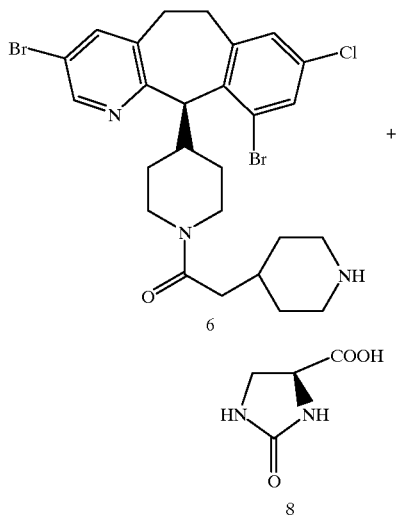

40
-continued

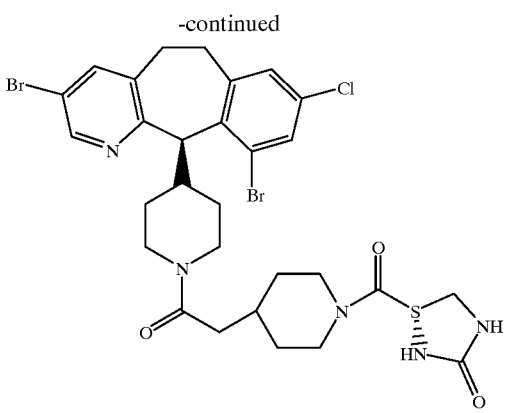

Dissolve 0.138 g (0.2325 mmol) of the product of Preparative Example 10 in 1.3 ml of DMF, stir at room temperature overnight, and add 0.074 g (0.73 mmol) of 4-methylmorpholine, 0.0552g (0.2879 mmol) of DEC, 0.0415 g (0.3071 mmol) of HOBT, and 0.0386 g 2-oxo-4 (S)-oxazolidine carboxylic acid (8) (0.294 mmole). Stir the mixture at room temperature for 2 days, then concentrate in vacuo to a residue and partition the residue between $CH_2Cl_2$ and water. Wash the organic phase successively with saturated $NaHCO_3$ (aqueous), and brine. Dry the organic phase over $MgSO_4$ and concentrate in vacuo to a residue. Thick layer chromatography of the residue (silica gel, 10% $CH_3OH/CH_2Cl_2+NH_3$) gives 0.123 g of the title compound. Mass Spec.: $MH^+707$; m.p.=170.3–177.2° C.

EXAMPLE 5

4-(3,10-Dibromo-8-chloro-6,11-dihydro-5H-benzo[5,6]cyclohepta[1,2-b]-pyridin-11-yl)-1-[(tetrahydro-2-oxo-5(R)-oxazolidin)]piperidine

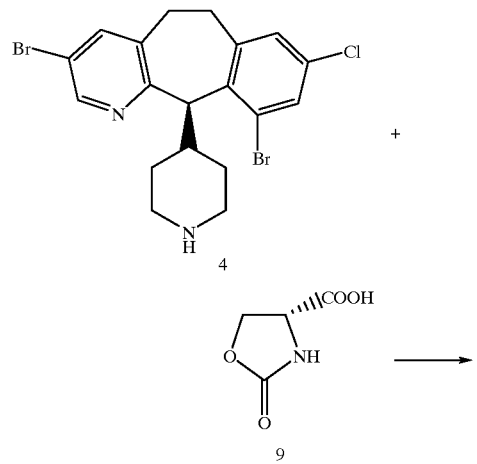

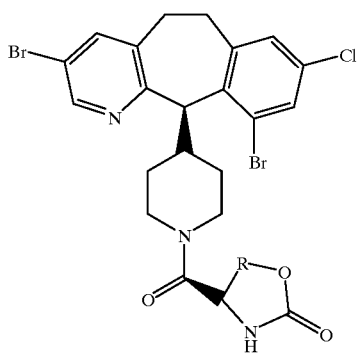

Dissolve 1 equivalent of the product of Preparative Example 5 (4) in DMF, stir at room temperature overnight, and add 3 equivalents of 4-methylmorpholine, 1.24 equivalents of DEC, 1.3 equivalents of HOBT, and 1.4 equivalents of 2-oxo-5(R)-oxazolidincarboxylic acid (9, prepared as described in *Synth. Comm.*, 25 (15),2285–2294, 1995). Stir the mixture at room temperature for 2 days, then concentrate in vacuo to a residue and partition the residue between $CH_2Cl_2$ and water. Wash the organic phase successively with saturated $NaHCO_3$ (aqueous), and brine. Dry the organic phase over $MgSO_4$ and concentrate in vacuo to a residue. Thick layer chromatography of the residue (silica gel, 10% $CH_3OH/CH_2Cl_2+NH_3$) gives the title compound.

EXAMPLE 6

4-(3,10-Dibromo-8-chloro-6,11-dihydro-5H-benzo[5,6]cyclohepta[1,2-b]pyridin-11-yl)-1-[(tetrahydro-2-oxo-5(S)oxazolidin)]piperidine

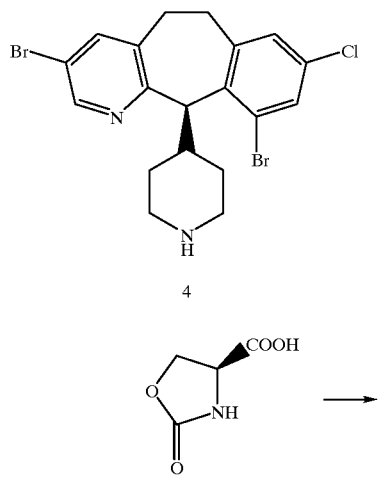

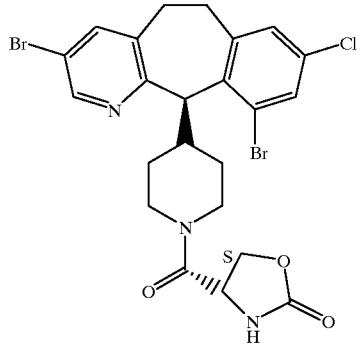

Use the procedure of Example 5, substituting 2-oxo-5(S)-oxazolidincarboxylic acid (7, prepared as described in *Bull. Chem. Soc.*, 974–979, 1968) for 9 to give the title compound.

EXAMPLE 7

4-(3,10-dibromo-8-chloro-6,11-dihydro-5H-benzo[5,6]cycloheptar[1,2-b]pyridin-11-yl)-1-[(tetrahydro-$^2$-oxo-($^4$R)imidazorlidinyl)]piperidine

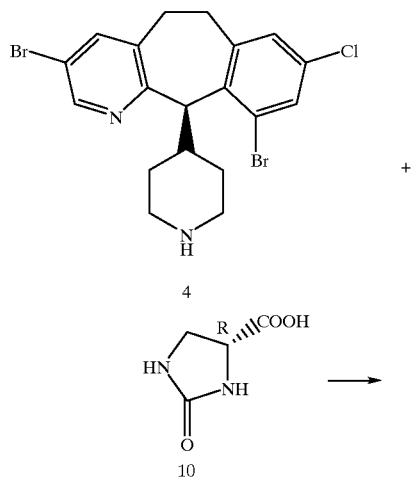

Use the procedure of Example 5, substituting 2-oxo-4(R)-imidazolidine carboxylic acid (10, prepared as described in *Synth. Comm.*, 22 (6),883–891, 1992) for 9 to give the title compound.

EXAMPLE 8

4-(3,10-Dibromo-8-chloro-6,11-dihydro-5H-benzo[5,6]cyclohepta[1,2-b]pyridin-11-yl)-1-[(tetrahydro-2-oxo-(4S)imidazolidinyl)]piperidine

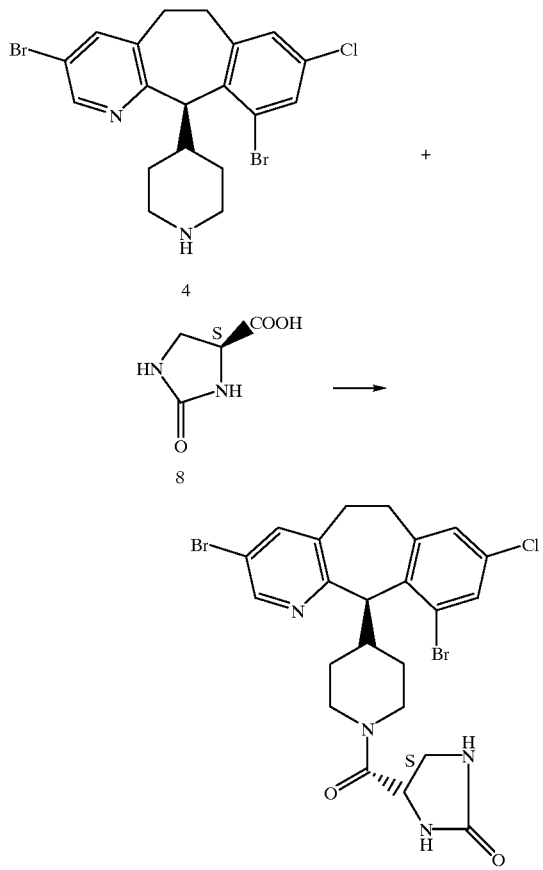

Use the procedure of Example 5, substituting 2-oxo-4(S)-imidazolidine carboxylic acid (8) for 9 to give the title compound.

EXAMPLE 9

4-(3,10-Dibromo-8-chloro-6,11-dihydro-5H-benzo[5,6]cyclohepta[1,2-b]pyridin-11-yl)-1-f(tetrahydro-2-oxo-5(S)oxazolidinyl)acetyl]piperidine

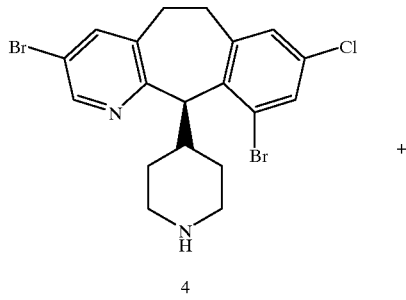

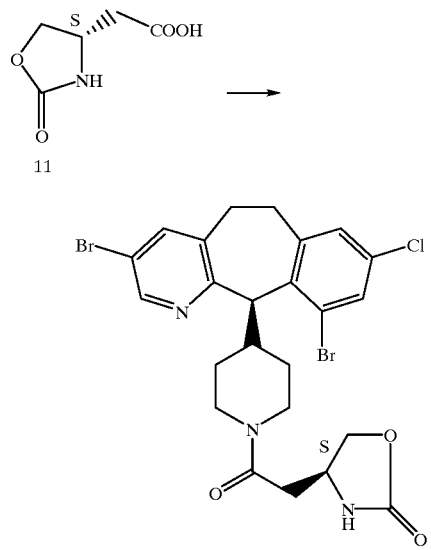

Use the procedure of Example 5, substituting 2-oxo-4(S)-oxazolidine acetic acid (11, prepared as described in *Synth. Comm.*, 25 (15), 2285–2294, 1995) for 9 to give the title compound.

EXAMPLE 10

4-(3,10-Dibromo-8-chloro-6,11-dihydro-5H-benzo[5,6]cyclohepta[1,2-b]pyridin-11-yl)-1-[(tetrahydro-2-oxo-5(R)oxazolidinyl)acetyl]piperidine

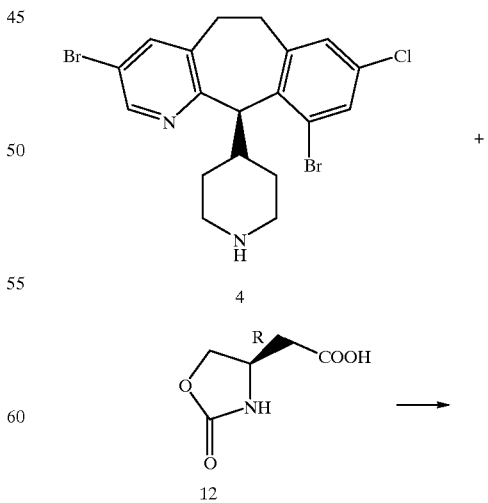

-continued

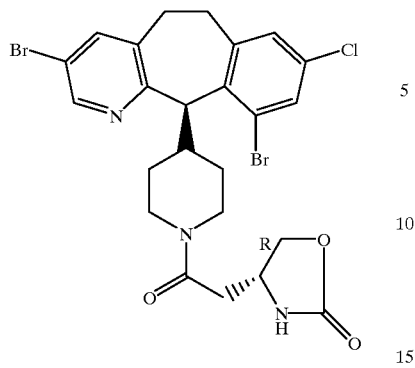

Use the procedure of Example 5, substituting 2-oxo-4(R)-oxazolidine acetic acid (12, prepared as described in *Synth. Comm.*, 25 (15), 2285–2294, 1995) for 9 to give the title compound.

EXAMPLE 11

4-(3,10-Dibromo-8-chloro-6,11-dihydro-5H-benzo[5,6]cyclohepta[1,2-b]pyridin-11-yl)-1-[(tetrahydro-2-oxo-5(R)oxazolidinyl)acetyl]piperidine

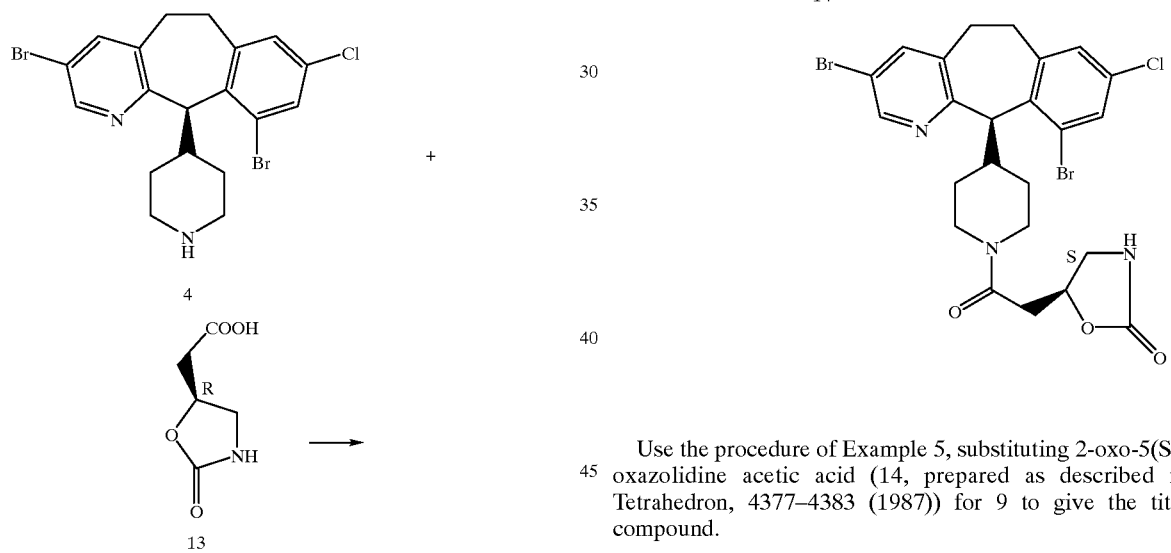

Use the procedure of Example 5, substituting 2-oxo-5(R)-oxazolidine acetic acid (13, prepared as described in Tetrahedron, 4377–4383(1987)) for 9 to give the title compound.

EXAMPLE 12

4-(3,10-Dibromo-8-chloro-6,11-dihydro-5H-benzo[5,6]cyclohepta[1,2-b]pyridin-11-yl)-1-[(tetrahydro-2-oxo-5(S)oxazolidinyl)acetyl]pipreridine

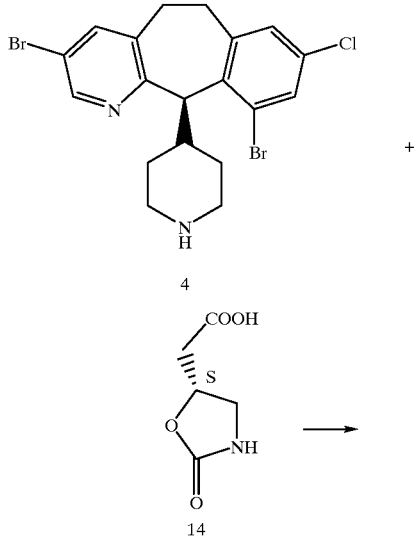

Use the procedure of Example 5, substituting 2-oxo-5(S)-oxazolidine acetic acid (14, prepared as described in Tetrahedron, 4377–4383 (1987)) for 9 to give the title compound.

EXAMPLE 13

4-(3,10-Dibromo-8-chloro-6,11-dihydro-5H-benzo[5,6]cyclohepta[1,2-b]pyridin-11-yl)-1-[(tetrahydro-2-oxo-(4S)imidazolidinyl)acetyl]piperidine

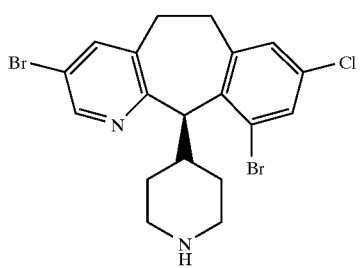

-continued

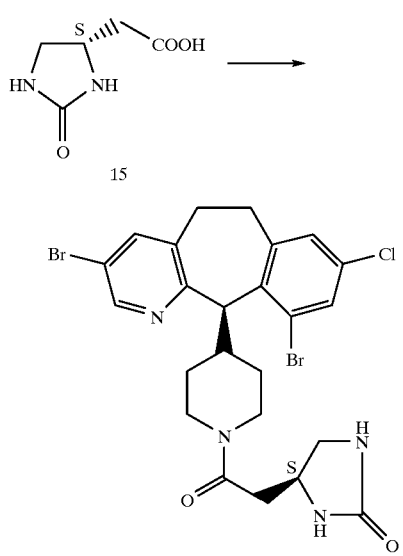

Use the procedure of Example 5, substituting 2-oxo-4(S)-imidazolidine acetic acid (15, prepared as described in *Synth. Comm.*, 22 (6), 883–891, 1992) for 9 to give the title compound.

EXAMPLE 14

4-(3,10-Dibromo-8-chloro-6,11-dihydro-5H-benzo[5,6]cyclohepta[1,2-b]pyridin-11-yl)-1-[(tetrahydro-2-oxo-(4R)imidazolidinyl)acetyl]piperidine

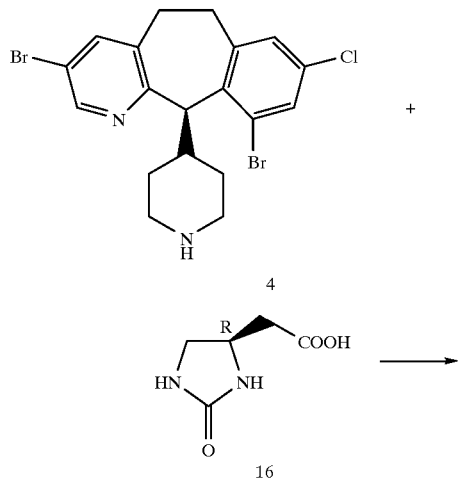

-continued

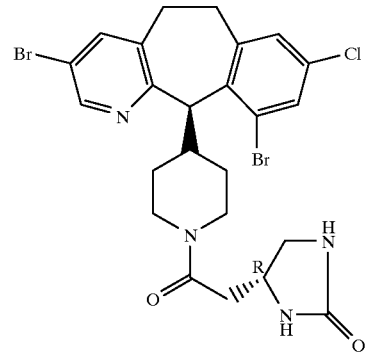

Use the procedure of Example 5, substituting 2-oxo-4(R)-imidazolidine acetic acid (16, prepared as described in *Synth. Comm.*, 22 (6), 883–891, 1992) for 9 to give the title compound.

EXAMPLE 15

4-(3,10-Dibromo-8-chloro-6,11-dihydro-5H-benzo[5,6]cyclohepta[1,2-b]pyridin-11-yl)-1-[(tetrahydro-2-oxo-4-piperidinylacetyl]piperidine

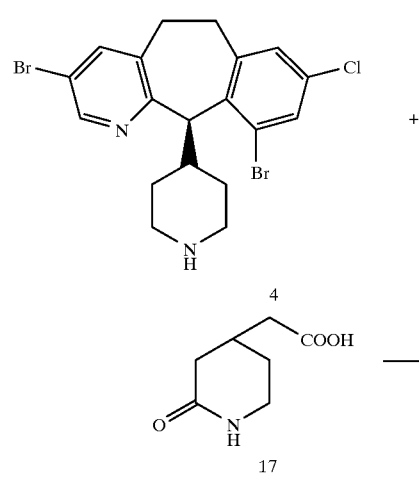

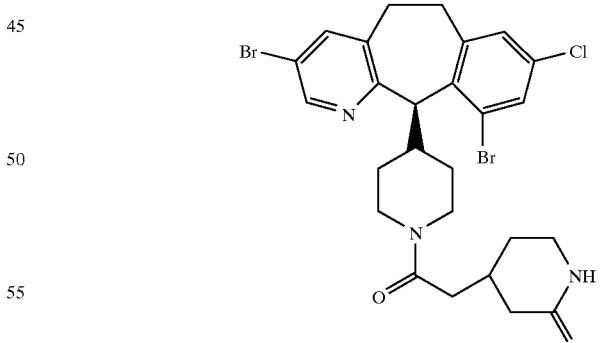

Use the procedure of Example 5, substituting 2-oxo-4-piperidine acetic acid (17, prepared as described in *Chem.Abstr.*, 53 (1959), col. 8111) for 9 to give the title compound.

EXAMPLE 16

4-(3,Dibromo-8-chloro-6,11-dihydro-5H-benzo[5,6]cyclohepta[1,2-b]pyridin-11-yl)-1-[(tetrahydro-2,5-dioxo-4-piperidinylacetyl]piperidine

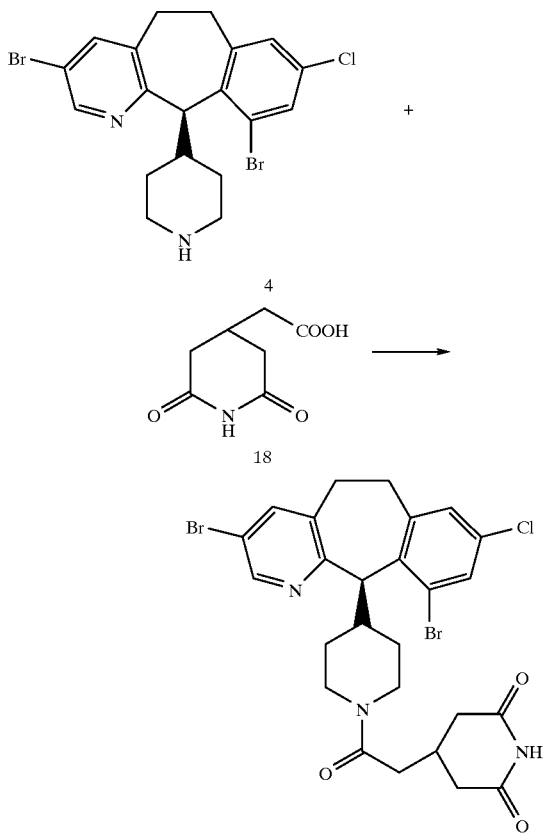

Use the procedure of Example 5, substituting 2,5-dioxo-4-piperidine acetic acid (18, prepared as described in *Chem. Abstr.*, 53 (1959), col. 21940) for 9 to give the title compound.

FPT $IC_{50}$ (inhibition of farnesyl protein transferase, in vitro enzyme assay), COS Cell $IC_{50}$ (Cell-Based Assay), GGPT $IC_{50}$ (inhibition of geranylgeranyl protein transferase, in vitro enzyme assay), Cell Mat Assay, and anti-tumor activity (in vivo anti-tumor studies) are determined by the assay procedures described in WO 95/10516.

The results are given in Table 1. In Table 1 "Ex. No." stands for "Example Number" and "nM" stands for "nanomolar"

| Ex. No. | FPT $IC_{50}$ (nM) | COS Cell $IC_{50}$ (nM) |
|---|---|---|
| 1 | 15 | 50 |
| 2 | 3.98 | 9 |
| 3 | 2.3 | 7 |
| 4 | 1.8 | 33 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

EXAMPLE A

Tablets

| No. | Ingredients | mg/tablet | mg/tablet |
|-----|-------------|-----------|-----------|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|     | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 1–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
|-----|------------|------------|------------|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|     | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the structural formula

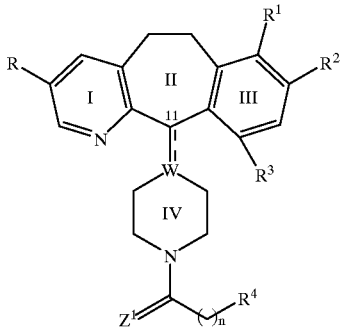

or an N-oxide thereof, or a pharmaceutically acceptable salt or solvate thereof, wherein:

R and $R^2$ are independently selected from halo;

$R^1$ and $R^3$ are independently selected from the group consisting of H and halo, provided that at least one of $R^1$ and $R^3$ is H;

W is CH or C, when the double bond is present at the C-11 position;

$R^4$ is selected from the group consisting of

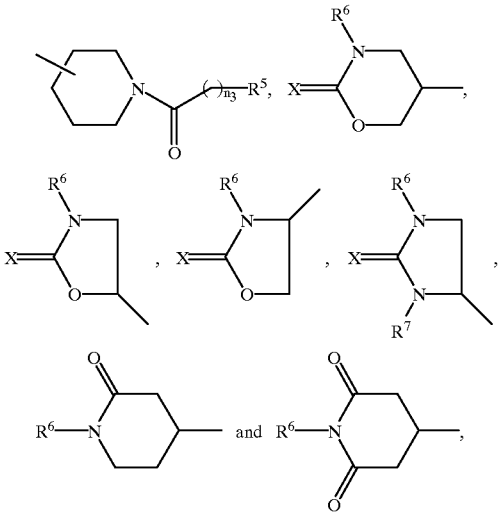

wherein $R^5$ is selected from the group consisting of

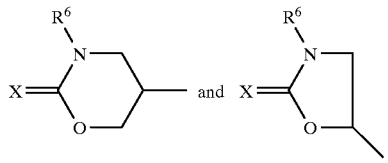

$R^6$ and $R^7$ are independently selected from the group consisting of H, alkyl, substituted alkyl, acyl, aryl, aralkyl, heterocycloalkyl and heteroaryl;

X is =O or =S;

$Z^1$ is =O; and n and $n_3$ are independently 0, 1 or 2.

2. A compound of claim 1, wherein X is =O and $R^6$ and $R^7$ are each hydrogen.

3. A compound of claim 2, wherein n is 1 and $n_3$ is 0 or 1.

4. A compound of claim 1, wherein R is bromo and $R^2$ is chloro or bromo.

5. A compound of claim 3, wherein R is bromo and $R^2$ is chloro or bromo.

6. A compound of claim 1, wherein R is bromo, $R^2$ is chloro or bromo, $R^1$ is H, and $R^3$ is chloro or bromo.

7. A compound of claim 3, wherein R is bromo, $R^2$ is chloro or bromo, $R^1$ is H, and $R^3$ is chloro or bromo.

8. A compound of claim 1, wherein R is bromo, $R^2$ is chloro or bromo, $R^3$ is H, and $R^1$ is chloro or bromo.

9. A compound of claim 3, wherein R is bromo, $R^2$ is chloro or bromo, $R^3$ is H, and $R^1$ is chloro or bromo.

10. A compound of claim 1 selected from the group consisting of

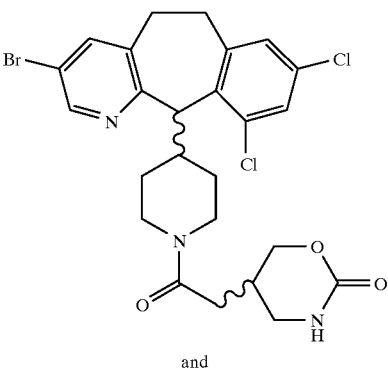

and

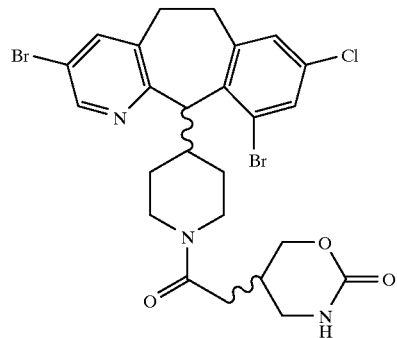

11. A method of treating tumor cells expressing an activated ras oncogene comprising administering a farnesyl transferase inhibiting amount of a compound of claim 1 to a mammal in need of such treatment.

12. A pharmaceutical composition for inhibiting farnesylation of ras protein, thereby inhibiting the abnormal growth of cells resulting from ras protein activation comprising an effective amount of a compound of claim 1 in combination with a pharmaceutically acceptable carrier.

13. A method of inhibiting farnesylation of ras protein, thereby inhibiting abnormal cell growth resulting from ras protein activation, comprising administering a farnesyl transferase inhibiting amount of a compound of claim 1 to a mammal in need of such treatment.

* * * * *